US012114959B2

(12) United States Patent (10) Patent No.: US 12,114,959 B2
Arnold et al. (45) Date of Patent: *Oct. 15, 2024

(54) SEDENTARY PERIOD DETECTION USING A WEARABLE ELECTRONIC DEVICE

(71) Applicant: Fitbit, Inc., San Francisco, CA (US)

(72) Inventors: Jacob Antony Arnold, Fremont, CA (US); Allison Maya Russell, Berkeley, CA (US); Zachariah Lord Wasson, II, Berkeley, CA (US); Shelten Gee Jao Yuen, Berkeley, CA (US)

(73) Assignee: FITBIT, INC., San Francisco, CA (US)

( * ) Notice: Subject to any disclaimer, the term of this patent is extended or adjusted under 35 U.S.C. 154(b) by 477 days.

This patent is subject to a terminal disclaimer.

(21) Appl. No.: 17/484,665

(22) Filed: Sep. 24, 2021

(65) Prior Publication Data

US 2022/0079440 A1 Mar. 17, 2022

Related U.S. Application Data

(63) Continuation of application No. 16/700,006, filed on Dec. 2, 2019, now Pat. No. 11,129,534, which is a
(Continued)

(51) Int. Cl.
*A61B 5/00* (2006.01)
*A61B 5/0205* (2006.01)
(Continued)

(52) U.S. Cl.
CPC ........ *A61B 5/0022* (2013.01); *A61B 5/02055* (2013.01); *A61B 5/1116* (2013.01);
(Continued)

(58) Field of Classification Search
CPC . A61B 5/02416; A61B 5/0533; A61B 5/1116; A61B 5/1118; A61B 5/1123;
(Continued)

(56) References Cited

U.S. PATENT DOCUMENTS 2,284,849 A 8/1941 Anderson et al.
2,717,736 A 9/1955 Schlesinger
(Continued)

FOREIGN PATENT DOCUMENTS

CN 101789933 A 7/2010
CN 101978374 2/2011
(Continued)

OTHER PUBLICATIONS

U.S. Office Action dated Aug. 3, 2016, in U.S. Appl. No. 15/052,405.
(Continued)

*Primary Examiner* — Scott Luan
(74) *Attorney, Agent, or Firm* — DORITY & MANNING P.A.

(57) ABSTRACT

Systems and methods for determining a sedentary state of a user are described. Sensor data is collected and analyzed to calculate metabolic equivalent of task (MET) measures for a plurality of moments of interest. Based on the MET measures and a time period for which the MET measures exceed a threshold value, it is determined whether the user is in a sedentary state. If the user is in the sedentary state, the user is provided a notification to encourage the user to perform a non-sedentary activity.

16 Claims, 8 Drawing Sheets

Related U.S. Application Data continuation of application No. 15/671,063, filed on Aug. 7, 2017, now Pat. No. 10,497,246, which is a continuation of application No. 15/078,981, filed on Mar. 23, 2016, now Pat. No. 9,728,059, which is a continuation-in-part of application No. 14/221,234, filed on Mar. 20, 2014, now Pat. No. 9,801,547, which is a continuation of application No. 14/156,413, filed on Jan. 15, 2014, now Pat. No. 9,241,635.

(60) Provisional application No. 62/137,750, filed on Mar. 24, 2015, provisional application No. 61/752,826, filed on Jan. 15, 2013.

(51) Int. Cl.
| | | |
|---|---|---|
| *A61B 5/11* | (2006.01) | |
| *G08B 21/04* | (2006.01) | |
| *G16H 20/30* | (2018.01) | |
| *G16H 20/40* | (2018.01) | |
| *G16H 40/63* | (2018.01) | |
| *A61B 5/021* | (2006.01) | |
| *A61B 5/024* | (2006.01) | |
| *A61B 5/0533* | (2021.01) | |
| *A61B 5/22* | (2006.01) | |
| *G01C 22/00* | (2006.01) | |

(52) U.S. Cl.
CPC ............ *A61B 5/681* (2013.01); *A61B 5/7264* (2013.01); *A61B 5/746* (2013.01); *G08B 21/0415* (2013.01); *G16H 20/30* (2018.01); *G16H 20/40* (2018.01); *G16H 40/63* (2018.01); *A61B 5/021* (2013.01); *A61B 5/02416* (2013.01); *A61B 5/0533* (2013.01); *A61B 5/1118* (2013.01); *A61B 5/1123* (2013.01); *A61B 5/222* (2013.01); *A61B 5/4809* (2013.01); *A61B 5/7267* (2013.01); *A61B 5/743* (2013.01); *A61B 2560/0209* (2013.01); *A61B 2560/0242* (2013.01); *A61B 2562/0219* (2013.01); *G01C 22/006* (2013.01)

(58) Field of Classification Search
CPC ....... A61B 5/222; A61B 5/4809; A61B 5/681; A61B 5/7264; A61B 5/7267; A61B 5/743; A61B 5/746; G01C 22/006; G06F 19/3481; G08B 21/0415; G16H 40/63
See application file for complete search history.

(56) References Cited

U.S. PATENT DOCUMENTS

| | | |
|---|---|---|
| 2,827,309 A | 3/1958 | Fred |
| 2,883,255 A | 4/1959 | Anderson |
| 3,163,856 A | 12/1964 | Kirby |
| 3,250,270 A | 5/1966 | Lyon |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,466,204 A | 8/1984 | Wu |
| 4,575,804 A | 3/1986 | Ratcliff |
| 4,578,769 A | 3/1986 | Frederick |
| 4,617,525 A | 10/1986 | Lloyd |
| 4,855,942 A | 8/1989 | Bianco |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,099,842 A | 3/1992 | Mannheimer et al. |
| 5,224,059 A | 6/1993 | Nitta et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,485,402 A | 1/1996 | Smith et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,692,324 A | 12/1997 | Goldston et al. |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,454,708 B1 | 9/2002 | Ferguson et al. |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,583,369 B2 | 6/2003 | Montagnino et al. |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,772,331 B1 | 8/2004 | Hind et al. |
| 6,788,200 B1 | 9/2004 | Jamel et al. |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 6,984,207 B1 | 1/2006 | Sullivan et al. |
| 7,020,508 B2 | 3/2006 | Stivoric et al. |
| 7,041,032 B1 | 5/2006 | Calvano |
| 7,062,225 B2 | 6/2006 | White |
| 7,099,237 B2 | 8/2006 | Lall |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |

(56) References Cited

U.S. PATENT DOCUMENTS

| | | |
|---|---|---|
| 7,261,690 B2 | 8/2007 | Teller et al. |
| 7,272,982 B2 | 9/2007 | Neuhauser et al. |
| 7,283,870 B2 | 10/2007 | Kaiser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,499,439 B2 | 3/2009 | Li et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shugg |
| 7,640,134 B2 | 12/2009 | Park et al. |
| 7,653,503 B2 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,827,000 B2 | 11/2010 | Stirling et al. |
| 7,865,140 B2 | 1/2011 | Levien et al. |
| 7,881,902 B1 | 2/2011 | Kahn et al. |
| 7,907,901 B1 | 3/2011 | Kahn et al. |
| 7,925,022 B2 | 4/2011 | Jung et al. |
| 7,927,253 B2 | 4/2011 | Vincent et al. |
| 7,941,665 B2 | 5/2011 | Berkema et al. |
| 7,942,824 B1 | 5/2011 | Kayyali et al. |
| 7,953,549 B2 | 5/2011 | Graham et al. |
| 7,959,539 B2 | 6/2011 | Takeishi et al. |
| 7,983,876 B2 | 7/2011 | Vock et al. |
| 8,005,922 B2 | 8/2011 | Boudreau et al. |
| 8,028,443 B2 | 10/2011 | Case, Jr. |
| 8,036,850 B2 | 10/2011 | Kulach et al. |
| 8,055,469 B2 | 11/2011 | Kulach et al. |
| 8,059,573 B2 | 11/2011 | Julian et al. |
| 8,060,337 B2 | 11/2011 | Kulach et al. |
| 8,095,071 B2 | 1/2012 | Sim et al. |
| 8,099,318 B2 | 1/2012 | Moukas et al. |
| 8,103,247 B2 | 1/2012 | Ananthanarayanan et al. |
| 8,132,037 B2 | 3/2012 | Fehr et al. |
| 8,172,761 B1 | 5/2012 | Rulkov et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,190,651 B2 | 5/2012 | Treu et al. |
| 8,213,613 B2 | 7/2012 | Diehl et al. |
| 8,260,261 B2 | 9/2012 | Teague |
| 8,270,297 B2 | 9/2012 | Akasaka et al. |
| 8,271,662 B1 | 9/2012 | Gossweiler, III et al. |
| 8,289,162 B2 | 10/2012 | Mooring et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,638,228 B2 | 1/2014 | Amico et al. |
| 8,670,953 B2 | 3/2014 | Yuen et al. |
| 8,684,900 B2 | 4/2014 | Tran |
| 8,690,578 B1 | 4/2014 | Nusbaum et al. |
| 8,712,723 B1 | 4/2014 | Kahn et al. |
| 8,734,296 B1 | 5/2014 | Brumback et al. |
| 8,738,321 B2 | 5/2014 | Yuen et al. |
| 8,738,323 B2 | 5/2014 | Yuen et al. |
| 8,738,925 B1 | 5/2014 | Park et al. |
| 8,744,803 B2 | 6/2014 | Park et al. |
| 8,762,101 B2 | 6/2014 | Yuen et al. |
| 8,764,651 B2 | 7/2014 | Tran |
| 8,825,445 B2 | 9/2014 | Hoffman et al. |
| 8,847,988 B2 | 9/2014 | Geisner et al. |
| 8,849,610 B2 | 9/2014 | Molettiere et al. |
| 8,868,377 B2 | 10/2014 | Yuen et al. |
| 8,892,401 B2 | 11/2014 | Yuen et al. |
| 8,909,543 B2 | 12/2014 | Tropper et al. |
| 8,949,070 B1 | 2/2015 | Kahn et al. |
| 8,954,290 B2 | 2/2015 | Yuen et al. |
| 8,961,414 B2 | 2/2015 | Teller et al. |
| 8,968,195 B2 | 3/2015 | Tran |
| 9,031,812 B2 | 5/2015 | Roberts et al. |
| 9,042,971 B2 | 5/2015 | Brumback et al. |
| 9,047,648 B1 | 6/2015 | Lekutai et al. |
| 9,062,976 B2 | 6/2015 | Tanabe |
| 9,066,209 B2 | 6/2015 | Yuen et al. |
| 9,081,534 B2 | 7/2015 | Yuen et al. |
| 9,113,823 B2 | 8/2015 | Yuen et al. |
| 9,167,991 B2 | 10/2015 | Yuen et al. |
| 9,241,635 B2 | 1/2016 | Yuen et al. |
| 9,288,298 B2 | 3/2016 | Choudhary et al. |
| 9,310,909 B2 | 4/2016 | Myers et al. |
| 9,374,279 B2 | 6/2016 | Yuen et al. |
| 9,426,769 B2 | 8/2016 | Haro |
| 9,629,558 B2 | 4/2017 | Yuen et al. |
| 9,728,059 B2 | 8/2017 | Arnold et al. |
| 9,801,547 B2 | 10/2017 | Yuen et al. |
| 10,004,406 B2 | 6/2018 | Yuen et al. |
| 10,080,530 B2 | 9/2018 | Cheng et al. |
| 10,497,246 B2 | 12/2019 | Arnold et al. |
| 10,588,519 B2 | 3/2020 | Yuen et al. |
| 2001/0049470 A1 | 12/2001 | Mault et al. |
| 2001/0055242 A1 | 12/2001 | Deshmukh et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0107575 A1 | 6/2003 | Cardno |
| 2003/0131059 A1 | 7/2003 | Brown et al. |
| 2003/0171189 A1 | 9/2003 | Kaufman |
| 2003/0176815 A1 | 9/2003 | Baba et al. |
| 2003/0208335 A1 | 11/2003 | Unuma et al. |
| 2003/0226695 A1 | 12/2003 | Mault |
| 2004/0054497 A1 | 3/2004 | Kurtz |
| 2004/0061324 A1 | 4/2004 | Howard |
| 2004/0116837 A1 | 6/2004 | Yamaguchi et al. |
| 2004/0117963 A1 | 6/2004 | Schneider |
| 2004/0122488 A1 | 6/2004 | Mazar et al. |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0186965 A1 | 8/2005 | Pagonis et al. |
| 2005/0187481 A1 | 8/2005 | Hatib |
| 2005/0195830 A1 | 9/2005 | Chitrapu et al. |
| 2005/0216724 A1 | 9/2005 | Isozaki |
| 2005/0228244 A1 | 10/2005 | Banet |

(56) References Cited

U.S. PATENT DOCUMENTS

| | | |
|---|---|---|
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064037 A1 | 3/2006 | Shalon et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0106535 A1 | 5/2006 | Duncan |
| 2006/0111944 A1 | 5/2006 | Sirmans et al. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0189863 A1 | 8/2006 | Peyser |
| 2006/0217231 A1 | 9/2006 | Parks et al. |
| 2006/0241521 A1 | 10/2006 | Cohen |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2006/0288117 A1 | 12/2006 | Raveendran et al. |
| 2007/0011028 A1 | 1/2007 | Sweeney |
| 2007/0049384 A1 | 3/2007 | King et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippo et al. |
| 2007/0083602 A1 | 4/2007 | Heggenhougen et al. |
| 2007/0123391 A1 | 5/2007 | Shin et al. |
| 2007/0135264 A1 | 6/2007 | Rosenberg |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0179761 A1 | 8/2007 | Wren et al. |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katragadda et al. |
| 2008/0059113 A1 | 3/2008 | Tsubata |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0109158 A1 | 5/2008 | Huhtala |
| 2008/0114829 A1 | 5/2008 | Button et al. |
| 2008/0125288 A1 | 5/2008 | Case |
| 2008/0125959 A1 | 5/2008 | Doherty |
| 2008/0129457 A1 | 6/2008 | Ritter et al. |
| 2008/0134102 A1 | 6/2008 | Movold et al. |
| 2008/0139910 A1 | 6/2008 | Mastrototaro et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0172204 A1 | 7/2008 | Nagashima et al. |
| 2008/0176655 A1 | 7/2008 | James et al. |
| 2008/0190202 A1 | 8/2008 | Kulach et al. |
| 2008/0214360 A1 | 9/2008 | Stirling et al. |
| 2008/0243432 A1 | 10/2008 | Kato et al. |
| 2008/0275309 A1 | 11/2008 | Stivoric et al. |
| 2008/0285805 A1 | 11/2008 | Luinge et al. |
| 2008/0287751 A1 | 11/2008 | Stivoric et al. |
| 2008/0300641 A1 | 12/2008 | Brunekreeft |
| 2009/0012418 A1 | 1/2009 | Gerlach |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0054737 A1 | 2/2009 | Magar et al. |
| 2009/0054751 A1 | 2/2009 | Babashan et al. |
| 2009/0058635 A1 | 3/2009 | LaLonde et al. |
| 2009/0063193 A1 | 3/2009 | Barton et al. |
| 2009/0063293 A1 | 3/2009 | Mirrashidi et al. |
| 2009/0076765 A1 | 3/2009 | Kulach et al. |
| 2009/0088183 A1 | 4/2009 | Piersol |
| 2009/0093341 A1 | 4/2009 | James et al. |
| 2009/0098821 A1 | 4/2009 | Shinya |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0299691 A1 | 12/2009 | Shimaoka et al. |
| 2009/0307517 A1 | 12/2009 | Fehr et al. |
| 2009/0309742 A1 | 12/2009 | Alexander et al. |
| 2009/0313857 A1 | 12/2009 | Carnes et al. |
| 2010/0023348 A1 | 1/2010 | Hardee et al. |
| 2010/0043056 A1 | 2/2010 | Ganapathy |
| 2010/0056208 A1 | 3/2010 | Ashida et al. |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0079291 A1 | 4/2010 | Kroll |
| 2010/0125729 A1 | 5/2010 | Baentsch et al. |
| 2010/0130873 A1 | 5/2010 | Yuen et al. |
| 2010/0158494 A1 | 6/2010 | King |
| 2010/0159709 A1 | 6/2010 | Kotani et al. |
| 2010/0167783 A1 | 7/2010 | Alameh et al. |
| 2010/0179411 A1 | 7/2010 | Holmström et al. |
| 2010/0185064 A1 | 7/2010 | Bandic et al. |
| 2010/0191153 A1 | 7/2010 | Sanders et al. |
| 2010/0205541 A1 | 8/2010 | Rapaport et al. |
| 2010/0217099 A1 | 8/2010 | LeBoeuf et al. |
| 2010/0222179 A1 | 9/2010 | Temple et al. |
| 2010/0259434 A1 | 10/2010 | Rud et al. |
| 2010/0261987 A1 | 10/2010 | Kamath et al. |
| 2010/0262045 A1 | 10/2010 | Heaton et al. |
| 2010/0292050 A1 | 11/2010 | Dibenedetto |
| 2010/0292600 A1 | 11/2010 | Dibenedetto et al. |
| 2010/0295684 A1 | 11/2010 | Hsieh et al. |
| 2010/0298656 A1 | 11/2010 | McCombie et al. |
| 2010/0298661 A1 | 11/2010 | McCombie et al. |
| 2010/0304674 A1 | 12/2010 | Kim et al. |
| 2010/0311544 A1 | 12/2010 | Robinette et al. |
| 2010/0331145 A1 | 12/2010 | Lakovic et al. |
| 2010/0331657 A1 | 12/2010 | Mensinger et al. |
| 2011/0003665 A1 | 1/2011 | Burton et al. |
| 2011/0009051 A1 | 1/2011 | Khedouri et al. |
| 2011/0021143 A1 | 1/2011 | Kapur et al. |
| 2011/0022349 A1 | 1/2011 | Stirling et al. |
| 2011/0029241 A1 | 2/2011 | Miller et al. |
| 2011/0032105 A1 | 2/2011 | Hoffman et al. |
| 2011/0051665 A1 | 3/2011 | Huang |
| 2011/0080349 A1 | 4/2011 | Holbein et al. |
| 2011/0087076 A1 | 4/2011 | Brynelsen et al. |
| 2011/0087137 A1 | 4/2011 | Hanoun |
| 2011/0092834 A1 | 4/2011 | Yazicioglu et al. |
| 2011/0106449 A1 | 5/2011 | Chowdhary et al. |
| 2011/0109540 A1 | 5/2011 | Milne et al. |
| 2011/0131005 A1 | 6/2011 | Ueshima et al. |
| 2011/0145894 A1 | 6/2011 | Garcia Morchon et al. |

(56) References Cited

U.S. PATENT DOCUMENTS

| | | |
|---|---|---|
| 2011/0153773 A1 | 6/2011 | Vandwalle |
| 2011/0167262 A1 | 7/2011 | Ross et al. |
| 2011/0193704 A1 | 8/2011 | Harper et al. |
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2011/0275940 A1 | 11/2011 | Nims et al. |
| 2012/0010822 A1 | 1/2012 | Kato et al. |
| 2012/0015778 A1 | 1/2012 | Lee et al. |
| 2012/0035487 A1 | 2/2012 | Werner et al. |
| 2012/0046113 A1 | 2/2012 | Ballas |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kääriäinen et al. |
| 2012/0116684 A1 | 5/2012 | Ingrassia, Jr. et al. |
| 2012/0119911 A1 | 5/2012 | Jeon et al. |
| 2012/0150483 A1 | 6/2012 | Vock et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0183939 A1 | 7/2012 | Aragones et al. |
| 2012/0203503 A1 | 8/2012 | Nakamura |
| 2012/0215328 A1 | 8/2012 | Schmelzer |
| 2012/0221634 A1 | 8/2012 | Treu et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0245716 A1 | 9/2012 | Srinivasan et al. |
| 2012/0254987 A1 | 10/2012 | Ge et al. |
| 2012/0265477 A1 | 10/2012 | Vock et al. |
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0289788 A1 | 11/2012 | Jain et al. |
| 2012/0290109 A1 | 11/2012 | Engelberg et al. |
| 2012/0296400 A1 | 11/2012 | Bierman et al. |
| 2012/0297229 A1 | 11/2012 | Desai et al. |
| 2012/0297440 A1 | 11/2012 | Reams et al. |
| 2012/0316406 A1 | 12/2012 | Rahman et al. |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1 | 5/2013 | Weast et al. |
| 2013/0114415 A1 | 5/2013 | Das et al. |
| 2013/0132501 A1 | 5/2013 | Vandwalle et al. |
| 2013/0151193 A1 | 6/2013 | Kulach et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0187789 A1 | 7/2013 | Lowe |
| 2013/0190008 A1 | 7/2013 | Vathsancam et al. |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0297220 A1 | 11/2013 | Yuen et al. |
| 2013/0310896 A1 | 11/2013 | Mass |
| 2013/0325396 A1 | 12/2013 | Yuen et al. |
| 2013/0331058 A1 | 12/2013 | Harvey |
| 2013/0337974 A1 | 12/2013 | Yanev et al. |
| 2013/0345978 A1 | 12/2013 | Lush et al. |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0085077 A1 | 3/2014 | Luna et al. |
| 2014/0094941 A1 | 4/2014 | Ellis et al. |
| 2014/0099614 A1 | 4/2014 | Hu et al. |
| 2014/0121471 A1 | 5/2014 | Walker |
| 2014/0125618 A1 | 5/2014 | Panther et al. |
| 2014/0135612 A1 | 5/2014 | Yuen et al. |
| 2014/0142466 A1 | 5/2014 | Kawabe et al. |
| 2014/0156228 A1 | 6/2014 | Yuen et al. |
| 2014/0164611 A1 | 6/2014 | Molettiere et al. |
| 2014/0176475 A1 | 6/2014 | Myers |
| 2014/0180022 A1 | 6/2014 | Stivoric et al. |
| 2014/0188431 A1 | 7/2014 | Barfield |
| 2014/0191866 A1 | 7/2014 | Yuen et al. |
| 2014/0200691 A1 | 7/2014 | Lee et al. |
| 2014/0206954 A1 | 7/2014 | Yuen et al. |
| 2014/0207264 A1 | 7/2014 | Quy |
| 2014/0213858 A1 | 7/2014 | Presura et al. |
| 2014/0221791 A1 | 8/2014 | Pacione et al. |
| 2014/0275885 A1 | 9/2014 | Isaacson et al. |
| 2014/0278229 A1 | 9/2014 | Hong et al. |
| 2014/0288435 A1 | 9/2014 | Richards et al. |
| 2014/0316305 A1 | 10/2014 | Venkatraman et al. |
| 2014/0337451 A1 | 11/2014 | Choudhary et al. |
| 2014/0337621 A1 | 11/2014 | Nakhimov |
| 2014/0343867 A1 | 11/2014 | Yuen et al. |
| 2015/0026647 A1 | 1/2015 | Park et al. |
| 2015/0057967 A1 | 2/2015 | Albinali |
| 2015/0088457 A1 | 3/2015 | Yuen et al. |
| 2015/0102923 A1 | 4/2015 | Messenger et al. |
| 2015/0120186 A1 | 4/2015 | Heikes |
| 2015/0127268 A1 | 5/2015 | Park et al. |
| 2015/0134268 A1 | 5/2015 | Yuen et al. |
| 2015/0137994 A1 | 5/2015 | Rahman et al. |
| 2015/0141873 A1 | 5/2015 | Fei |
| 2015/0198460 A1 | 7/2015 | Yamato et al. |
| 2015/0220883 A1 | 8/2015 | B'far et al. |
| 2015/0289802 A1 | 10/2015 | Thomas et al. |
| 2015/0324541 A1 | 11/2015 | Cheung et al. |
| 2015/0374267 A1 | 12/2015 | Laughlin |
| 2016/0058331 A1 | 3/2016 | Keen et al. |
| 2016/0058372 A1 | 3/2016 | Raghuram et al. |
| 2016/0061626 A1 | 3/2016 | Burton et al. |
| 2016/0063888 A1 | 3/2016 | McCallum et al. |
| 2016/0089572 A1 | 3/2016 | Liu et al. |
| 2016/0107646 A1 | 4/2016 | Kolisetty et al. |
| 2016/0150978 A1 | 6/2016 | Yuen et al. |
| 2016/0166156 A1 | 6/2016 | Yuen et al. |
| 2016/0203691 A1 | 7/2016 | Arnold et al. |
| 2016/0259426 A1 | 9/2016 | Yuen et al. |

(56) References Cited

U.S. PATENT DOCUMENTS

| | | | |
|---|---|---|---|
| 2016/0278669 | A1 | 9/2016 | Messenger et al. |
| 2016/0285985 | A1 | 9/2016 | Molettiere et al. |
| 2016/0323401 | A1 | 11/2016 | Messenger et al. |
| 2017/0238881 | A1 | 8/2017 | Cheng et al. |
| 2017/0239523 | A1 | 8/2017 | Cheng et al. |
| 2017/0243056 | A1 | 8/2017 | Cheng et al. |
| 2018/0055376 | A1 | 3/2018 | Yuen et al. |
| 2018/0061204 | A1 | 3/2018 | Arnold et al. |
| 2019/0059744 | A1 | 2/2019 | Yuen et al. |
| 2019/0392727 | A1 | 12/2019 | Cheng et al. |

FOREIGN PATENT DOCUMENTS

| | | |
|---|---|---|
| CN | 102067560 A | 5/2011 |
| CN | 102111434 | 6/2011 |
| CN | 102377815 | 3/2012 |
| CN | 102740933 | 10/2012 |
| CN | 102983890 | 3/2013 |
| CN | 103226647 | 7/2013 |
| CN | 203721002 | 7/2014 |
| EP | 1721237 | 8/2012 |
| JP | 11347021 | 12/1999 |
| RU | 2178588 | 1/2002 |
| WO | WO 2002/011019 | 2/2002 |
| WO | WO 2006/055125 | 5/2006 |
| WO | WO 2006/090197 | 8/2006 |
| WO | WO 2008/038141 | 4/2008 |
| WO | WO 2009/042965 | 4/2009 |
| WO | WO 2012/061438 | 5/2012 |
| WO | WO 2012/170586 | 12/2012 |
| WO | WO 2012/170924 | 12/2012 |
| WO | WO 2012/171032 | 12/2012 |
| WO | WO 2015/127067 | 8/2015 |
| WO | WO 2016/003269 | 1/2016 |

OTHER PUBLICATIONS

U.S. Notice of Allowance dated Dec. 2, 2016, in U.S. Appl. No. 15/052,405.
U.S. Office Action dated Jun. 30, 2017, in U.S. Appl. No. 15/052,405.
U.S. Office Action dated May 21, 2015, in U.S. Appl. No. 14/156,413.
U.S. Notice of Allowance dated Sep. 14, 2015, in U.S. Appl. No. 14/156,413.
U.S. Office Action dated Dec. 19, 2014, in U.S. Appl. No. 14/221,234.
U.S. Final Office Action dated Oct. 7, 2015, in U.S. Appl. No. 14/221,234.
U.S. Final Office Action dated Jun. 3, 2016, in U.S. Appl. No. 14/221,234.
U.S. Final Office Action dated Dec. 7, 2016, in U.S. Appl. No. 14/221,234.
U.S. Notice of Allowance dated Jun. 30, 2017, in U.S. Appl. No. 14/221,234.
U.S. Office Action dated May 18, 2016, in U.S. Appl. No. 15/016,712.
U.S. Final Office Action dated Oct. 7, 2016, in U.S. Appl. No. 15/016,712.
U.S. Office Action dated Jun. 29, 2017, in U.S. Appl. No. 15/016,712.
U.S. Notice of Allowance dated Dec. 19, 2017, in U.S. Appl. No. 15/016,712.
U.S. Office Action dated Jun. 7, 2019, in U.S. Appl. No. 16/017,870.
U.S. Notice of Allowance dated Nov. 4, 2019, in U.S. Appl. No. 16/017,870.
U.S. Office Action dated Jun. 1, 2016, in U.S. Appl. No. 15/078,981.
U.S. Final Office Action dated Sep. 8, 2016, in U.S. Appl. No. 15/078,981.
U.S. Notice of Allowance dated Apr. 4, 2017, in U.S. Appl. No. 15/078,981.
U.S. Office Action dated Aug. 9, 2018, in U.S. Appl. No. 15/671,063.
U.S. Final Office Action dated Feb. 7, 2019, in U.S. Appl. No. 15/671,063.
U.S. Notice of Allowance dated Jul. 11, 2019, in U.S. Appl. No. 15/671,063.
U.S. Office Action dated May 26, 2016, in U.S. Appl. No. 15/048,972.
U.S. Final Office Action dated Aug. 10, 2016, in U.S. Appl. No. 15/048,972.
U.S. Office Action dated Jun. 7, 2017, in U.S. Appl. No. 15/048,972.
U.S. Office Action dated Nov. 19, 2019, in U.S. Appl. No. 16/414,780.
U.S. Final Office Action dated Apr. 27, 2020, in U.S. Appl. No. 16/414,780.
U.S. Office Action dated Apr. 26, 2016, in U.S. Appl. No. 15/048,980.
U.S. Final Office Action dated Dec. 1, 2016, in U.S. Appl. No. 15/048,980.
U.S. Office Action dated Jul. 6, 2017, in U.S. Appl. No. 15/048,980.
U.S. Final Office Action dated Dec. 21, 2017, in U.S. Appl. No. 15/048,980.
U.S. Notice of Allowance dated May 21, 2018, in U.S. Appl. No. 15/048,980.
U.S. Corrected Notice of Allowability dated Jul. 2, 2018, in U.S. Appl. No. 15/048,980.
International Search Report issued on Aug. 15, 2008, in related application No. PCT/IB07/03617.
Chinese First Office Action dated Jul. 6, 2018, in Application No. 201610172515.9.
Chinese Second Office Action dated Jan. 2, 2019, in Application No. 201610172515.9.
"Activity Classification Using Realistic Data From Wearable Sensors", Parkka, et al., IEEE Transactions on Information Technology in Biomedicine, vol. 10, No. 1, Jan. 2006, pp. 119-128.
"Altimeter and Barometer System", Clifford, et al., Freescale Semiconductor Application Note AN1979, Rev. 3, Nov. 2006.
"Automatic classification of ambulatory movements and evaluation of energy consumptions utilizing accelerometers and barometer", Ohtaki, et al., Microsystem Technologies, vol. 11, No. 8-10, Aug. 2005, pp. 1034-1040.
Chandrasekar et al., "Plug-and-Play, Single-Cip Photoplethysmography," 34th Annual International Conference of the IEEE EMBS, San Diego, California, USA, Aug. 28-Sep. 1, 2012. 4 pages.
"Classification of Human Moving Patterns Using Air Pressure and Acceleration", Sagawa, et al., Proceedings of the 24.sup.th Annual Conference of the IEEE Industrial Electronics Society, vol. 2, Aug.-Sep. 1998, pp. 1214-1219.
Definition of "Graphic" from Merriam-Webster Dictionary, downloaded from merriam-webster.com on Oct. 4, 2014.
Definition of "Graphical user interface" from Merriam-Webster Dictionary, downloaded from merriam-webster.com on Oct. 4, 2014.
"Design of a Wireless Assisted Pedestrian Dead Reckoning System—The NavMote Experience", Fang, et al., IEEE Transactions on Instrumentation and Measurement, vol. 54, No. 6, Dec. 2005, pp. 2342-2358.
"Direct Measurement of Human Movement by Accelerometry", Godfrey, et al., Medical Engineering & Physics, vol. 30, 2008, pp. 1364-1386.
"Drift-free dynamic height sensor using MEMS IMU aided by MEMS pressure sensor", Tanigawa, et al., Workshop on Positioning, Navigation and Communication, Mar. 2008, pp. 191-196.
"Evaluation of a New Method of Heading Estimation of Pedestrian Dead Reckoning Using Shoe Mounted Sensors", Stirling et al., Journal of Navigation, vol. 58, 2005, pp. 31-45.
"Fitbit Automatically Tracks Your Fitness and Sleep" published online at web.archive.org/web/20080910224820/http://www.fitbit.com, downloaded Sep. 10, 2008, 1 page.
"Foot Mounted Inertia System for Pedestrian Naviation", Godha et al., Measurement Science and Technology, vol. 19, No. 7, May 2008, pp. 1-9.
"A Hybrid Discriminative/Generative Approach for Modeling Human Activities", Lester, et al., Proc. of the Int'l Joint Conf. Artificial Intelligence, 2005, pp. 766-772.
"Improvement of Walking Speed Prediction by Accelerometry and Altimetiy, Validated by Satellite Positioning", Perrin, et al., Medical & Biological Engineering & Computing, vol. 38, 2000, pp. 164-168.
"Indoor Navigation with MEMS Sensors", Lammel, et al., Proceedings of the Eurosensors XIII conference, vol. 1, No. 1, Sep. 2009, pp. 532-535.

(56) References Cited

OTHER PUBLICATIONS

"An Intelligent Multi-Sensor system for Pedestrian Navigation", Retscher, Journal of Global Positioning Systems, vol. 5, No. 1, 2006, pp. 110-118.

Lee, Suevon, "Jawbone Gets 2 Patents Nixed In Fitbit Infringement Suit," Mar. 3, 17; retrieved from URL https://www.law360.com/articles/898111/jawbone-gets-2-patents-nixed-in-fitbit-infringement-suit on May 22, 17.

Minetti et al. Energy cost of walking and running at extreme uphill and downhill slopes. J Appl Physiol 2002; 93: 10-39-1046.

"Non-restricted measurement of walking distance", Sagawa, et al., IEEE Int'l Conf. on Systems, Man, and Cybernetics, vol. 3, Oct. 2000, pp. 1847-1852.

O'Donovan et al., 2009, A context aware wireless body area network (BAN), Proc. 3rd Intl. Conf. Pervasive Computing Technologies for Healthcare, pp. 1-8.

"On Foot Navigation: When GPS alone is not Enough", Ladetto, et al., Journal of Navigation, vol. 53, No. 2, Sep. 2000, pp. 279-285.

"SCP 1000-D01/D11 Pressure Sensor as Barometer and Altimeter", VTI Technologies Application, Jun. 2006, Note 33.

"Specification of the Bluetooth.RTM. System", Core Package version 4.1 Dec. 2013 vol. 0 and vol. 1, 283 pp.

"Suunto LUMI User Guide", Jun. and Sep. 1997.

Thompson et al., (Jan. 1996) "Predicted and measured resting metabolic rate of male and female endurance athletes," Journal of the American Dietetic Association 96(1): 30-34.

"Using MS5534 for altimeters and barometers", Intersema App., Note AN501, Jan. 2006.

"Validated caloric expenditure estimation using a single body-worn sensor", Lester, et al., Proc. of the Int'l Conf. on Ubiquitous Computing, 2009, pp. 225-234.

SEDENTARY PERIOD DETECTION USING A WEARABLE ELECTRONIC DEVICE

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD

Embodiments described in the present disclosure relate to the field of wearable electronic devices. Specifically, the embodiments relate to automatic detection of sedentary periods and promotion of non-sedentary behavior utilizing a wearable electronic device.

BACKGROUND

Trackers have gained popularity among consumers. A tracker is used to track a user's activities using a variety of sensors and helps the user to maintain a healthy life style. In order to determine the activities, the tracker collects activity data and runs computations on that data. One difficulty of obtaining accurate determinations of the activities is that the trackers, because they are worn by a user, are typically packaged in a compact casing containing less powerful processor(s) on which it is harder to run complex computations than larger electronic devices.

Another challenge in tracking the activities is differentiating between the user being stationary but performing an activity and the user being sedentary, e.g., spending minimal energy expenditure, etc. To illustrate, the user spends minimal energy when the user is seated, or seated and typing at a computer. Increased total sedentary time and longer sustained sedentary periods are associated with poor health and fitness, e.g., obesity, metabolic disorders, etc.

SUMMARY

In some embodiments, a wearable electronic device to be worn by a user is described. The wearable electronic device includes a set of one or more sensors to generate sensor data associated with the user when the user is wearing the wearable electronic device. The wearable electronic device further includes a set of one or more processors coupled to the set of sensors and a non-transitory machine readable storage medium coupled to the set of one or more processors and having stored therein instructions. When the instructions are executed by the set of one or more processors, the instructions cause the wearable electronic device to track a period of time during which a state of the user is determined to be sedentary. The determination is based on metabolic equivalent of task (MET) measures at moments of interest and the MET measures are calculated based on the sensor data. The instructions further cause the user to receive a notification responsive to the tracked period of time to encourage the user to limit the length of sedentary periods.

In various embodiments, the instructions further cause the wearable electronic device to classify, for each of the moments of interest, a status of the user as being sedentary or non-sedentary based on a MET measure for that moment of interest.

In several embodiments, a period of time is tracked based on a determination of contiguous ones of the moments of interest for which the status of the user is classified as sedentary.

In some embodiments, the status of the user at a moment of interest is classified as sedentary when a MET measure for that moment of interest is below a threshold MET value.

In various embodiments, the status of the user at a moment of interest is classified as sedentary when a MET measure for that moment of interest is between a first threshold value and a second threshold value, and the moment of interest is preceded by a first moment of interest within a threshold window of time for which the status of the user is sedentary, and is followed within the threshold window of time by a second moment of interest for which the status of the user is sedentary.

In some embodiments, one of the one of more sensors is a photoplethysmographic (PPG) sensor, and the MET measures are based on heart rate measures of the user calculated based on PPG sensor data.

In various embodiments, the instructions cause the wearable electronic device to filter out a period of time at which the state of the user is asleep.

In some embodiments, the wearable electronic device includes a sensor to generate sensor data associated with the user when the user is wearing the wearable electronic device. The wearable electronic device further includes a set of one or more processors coupled to the sensor and a non-transitory machine readable storage medium coupled to the set of one or more processors and having stored instructions therein. The instructions when executed by the set of one or more processors, cause the wearable electronic device to track a period of time during which the state of the user is determined to be sedentary based on the sensor data. The period of time has a beginning and an end. The instructions further cause the wearable electronic device to detect, responsive to the end of the period of time, that the state of the user has changed from sedentary to non-sedentary for a threshold period of time. The instructions cause the wearable device to cause the user to receive a notification responsive to the detection to encourage the user to remain non-sedentary.

In several embodiments, a notification is a message displayed on a display device of the wearable electronic device, or a vibration of the wearable electronic device, or a sound emitted by the wearable electronic device.

In some embodiments, a notification is indicative of the user having ended the period of time during which the state of the user is sedentary.

In various embodiments, a notification is determined based on preferences set by the user.

In some embodiments, a notification is a motivational statement displayed on the display device of the wearable electronic device.

In various embodiments, an apparatus to improve an effectiveness of notifications provided to the user of the wearable electronic device is described. The apparatus includes an electronic device including a sedentary state monitor to notify the user of the wearable electronic device to encourage the user to alter his/her sedentary behavior based on tracking periods of time during which the user is sedentary. The sedentary state monitor includes a set of one or more managers to receive a current state from a plurality of states of the user during periods of time. The states include a sedentary state. The one or more managers cause the wearable electronic device to receive notifications based on the current state to notify the user to limit a length of time during which the user is in the sedentary state.

In some embodiments, the apparatus further includes a sedentary learning unit coupled to receive data from each of the one or more managers concerning the notifications. The sedentary learning unit is coupled to a set of one or more sensors of the wearable electronic device to determine which notifications has an effect of modifying the sedentary behavior of the user, and to determine an updated configuration of at least one of the one or more managers. The updated configuration improves the user's response to the notifications to limit a length of a period of time during which the user is in the sedentary state.

In various embodiments, the one or more managers include a sedentary alert manager that receives a period of time for the current state of the user. The sedentary alert manager generates a sedentary alert based on a detection that the period of time exceeds a sedentary period of time threshold value. The sedentary alert manager sends a notification to the wearable electronic device indicating that the period of time exceeds the sedentary period of time threshold value.

In some embodiments, the one or more managers further include a non-sedentary state transition manager to receive the current state of the user. The non-sedentary state transition manager generates a notification that is based on a detection of an end of a sedentary period of time for the current state. The notification is sent from the non-sedentary state transition manager to the wearable electronic device.

In various embodiments, the sedentary learning unit determines based on notification information received from the sedentary alert manager and the non-sedentary state transition manager an updated configuration of at least one of the sedentary alert manager and the non-sedentary state transition manager. The updated configuration improves the user's response to the notification information to limit a length of a sedentary period of time during which the user is in the sedentary state.

In some embodiments, the updated configuration includes disabling at least one of the sedentary alert manager and the non-sedentary state transition manager.

In several embodiments, the sedentary learning unit includes a decision tree, a random forest, a support vector machine, neural network, a K-nearest neighbor, a Naïve Bayes, or Hidden Markov models.

In various embodiments, the sedentary learning unit allows the user to snooze a notification.

In some embodiments, the sedentary learning unit uses data related to the snoozed notification to determine an updated configuration of at least one of the one or more managers.

In various embodiments, the electronic device is a wearable electronic device.

BRIEF DESCRIPTION OF THE DRAWINGS

Embodiments described in the present disclosure are illustrated by way of example, and not by way of limitation, in the figures of the accompanying drawings in which like references indicate similar elements.

DETAILED DESCRIPTION

Figure 1A:
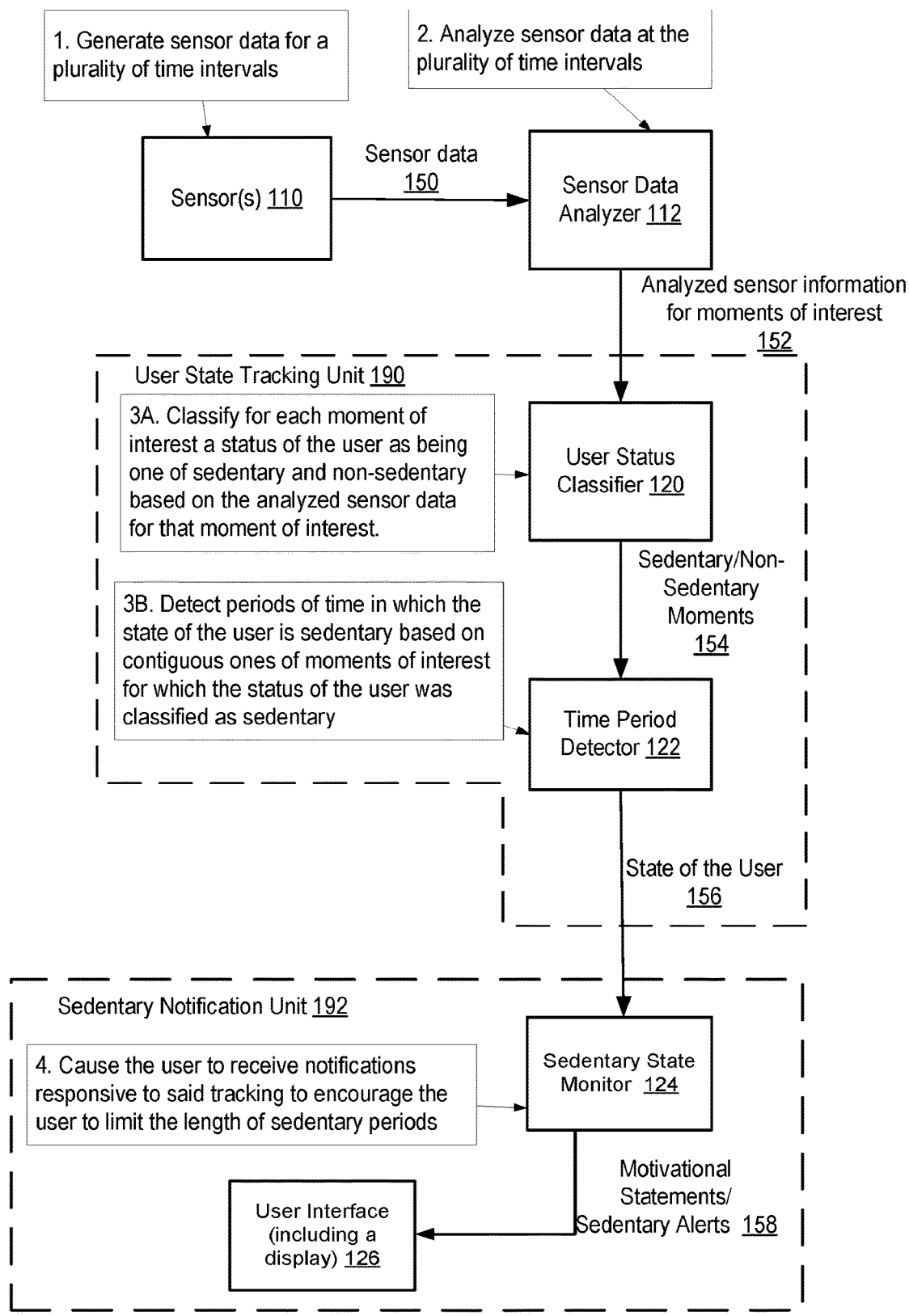
FIG. 1A illustrates sedentary user state detection and sedentary alert management, according to various embodiments described in the present disclosure.

In the following description, numerous specific details are set forth. However, it is understood that embodiments described in the present disclosure may be practiced without these specific details. In other instances, well-known circuits, structures and techniques have not been shown in detail in order not to obscure an understanding of the embodiments. It will be appreciated, however, by one skilled in the art that the embodiments may be practiced without such specific details. Those of ordinary skill in the art, with a description of the embodiments, will be able to implement appropriate functionality of the embodiments without undue experimentation.

In some embodiments, the terms "coupled" and "connected," along with their derivatives, are used. It should be understood that these terms are not intended as synonyms for each other. For example, "coupled" is used to indicate that two or more elements, which are or are not in direct physical or electrical contact with each other, co-operate or interact with each other. Moreover, in this example, "connected" is used to indicate an establishment of communication between two or more elements that are coupled with each other. Furthermore, in various embodiments, a "set", as used herein, refers to any positive whole number of items, including one item, unless stated otherwise, such as, a set of zero or more.

In some embodiments, an electronic device stores a code internally and/or transmits the code to other electronic devices over a computer network. The code is composed of software instructions and is sometimes referred to as computer program code or a computer program stored within a machine-readable storage media. In some embodiments, the code includes data for execution of the code. In various embodiments, the machine-readable storage media is computer-readable media. Examples of the computer-readable media include magnetic disks, optical disks, read only memory (ROM), random access memory (RAM), flash memory devices, phase change memory, etc. In various embodiments, the code is sent using a machine-readable transmission media, also called a carrier, such as, for example, electrical, optical, radio, acoustical, or other form of propagated signals. Further examples of the carrier include carrier waves, infrared signals, etc.

In various embodiments, the electronic device, e.g., a computer, etc., includes hardware and software. For example, the electronic device includes one or more processors coupled to one or more machine-readable storage media to store the code for execution on the one or more processors and/or to store data. To further illustrate, the electronic device includes a non-volatile memory containing the code and the non-volatile memory stores the code or data even when the electronic device is turned off, e.g., when power to the electronic device is removed, etc. While the electronic device is turned on, a part of the code that is to be executed by the one or more processors of the electronic device is copied from the non-volatile memory into a volatile memory, e.g., a dynamic random access memory (DRAM), a static random access memory (SRAM), etc., of the electronic device. The non-volatile memory is slower to access than the volatile memory. The electronic device typically also includes a set of one or more network interface(s), e.g., a network interface controller, a network interface card, an Internet access card, an Internet access controller, etc., each of which establishes physical or wireless network connections with the other electronic devices to communicate the code and/or data using the propagated signals. A wearable electronic device (WED), further described in detail below, is an example of the electronic device. It should be noted that one or more parts of an embodiment described in the present disclosure may be implemented using different combinations of software, firmware, and/or hardware.

Embodiments describing tracking of a sedentary state of a user and generation of a sedentary notification follow.

FIG. 1A illustrates sedentary state detection and sedentary alert management, according to some embodiments described in the present disclosure. It should be noted that task boxes 1, 2, 3A, 3B, and 4 of FIG. 1A are executed and components 110, 112, 120, 122, 124, and 126 of FIG. 1A are implemented, in some embodiments, in the wearable electronic device, or distributed between the wearable electronic device and one or more of the other electronic devices coupled to the wearable electronic device. In some embodiments, the wearable electronic device is worn on a body part, e.g., an arm, a wrist, an ankle, or a chest, etc., of the user, or embedded in a garment worn by the user. Examples of the one or more other electronic devices include a server including hardware and software, a tablet, a smartphone, a desktop computer, a laptop computer, and a smart television. In some embodiments, the one or more other electronic devices execute an application, sometimes referred to as an app, to implement, for example, a sensor data analyzer 112, a user state tracking unit 190, and/or a sedentary notification unit 192.

The task boxes 1-4 illustrate an order in which operations are performed by the components 110, 112, 120, 122, 124, and 126. As illustrated by the task box 1, one or more sensors 110 generate sensor data 150 for a plurality of time intervals. For example, the one or more sensors 110 are implemented in the wearable electronic device, such that, when worn by the user, at least some of the sensor data is indicative of an activity performed by the user. An example of the sensor data includes biometric data. In some embodiments, the one or more sensors 110 that generate the sensor data 150 include a motion sensor, e.g., a three axis accelerometer, etc. The motion sensor generates motion sensor data indicative of a motion, e.g., a number of steps taken by, a number of floors climbed by, a number of floors descended by, etc., of the user. In various embodiments, the one or more sensors 110 include a heart rate sensor, e.g., a photoplethysmographic (PPG) sensor, etc., to generate heart sensor data, e.g., PPG sensor data, etc., indicative of a heart rate of the user. In several embodiments, both the motion sensor and the heart rate sensor are housed in the same wearable electronic device or in different wearable electronic devices. In some embodiments, other types of sensors, e.g., a gyroscope, a gravity sensor, a rotation vector sensor, a magnetometer, a temperature sensor to measure a temperature of the user's skin and/or an environment surrounding the user, an ambient light sensor to measure an ambient light of the environment, a galvanic skin response sensor, a capacitive sensor, a humidity sensor, a sound sensor, etc., are housed in the wearable electronic device or in multiple wearable electronic devices. Examples of the environment surrounding the user include a room in which the user is situated, a street on which the user is standing or driving, an interior of a vehicle in which the user is situated, etc. In several embodiments, some or all of the sensor data 150 is generated by one of the one or more other electronic devices described above and received by the wearable electronic device from the one of the one or more other electronic devices.

The sensor data 150 generated during a time interval is processed by the sensor data analyzer 112. In some embodiments, a subset of the sensor data 150 is generated by performing a statistical operation, e.g., averaging, etc., on the sensor data 150 and is processed by the sensor data analyzer 112. At the task box 2, the sensor data analyzer 112 analyzes the sensor data 150 received from the one or more sensors 110 and calculates analyzed sensor information 152 for each moment of interest, and the analyzed sensor information 152 is used to determine a status, e.g., sedentary status or non-sedentary status, etc., of the user. In some embodiments, the analyzed sensor information 152 is calculated for a plurality of moments of interest at regular intervals of time, e.g., an interval within a range of 30 seconds-1.5 minute, a 1 minute interval, an interval within a range of 0.5 second-1.5 seconds, a 1 second interval, etc. In various embodiments, the intervals of time are configurable and dynamically adjusted, e.g., reduced or increased based on various factors, etc., and/or capable of being automatically disabled and/or manually disabled by the user for spans of time to save power.

In some embodiments, the analyzed sensor information 152 is metabolic equivalent of task (MET) measures, where each MET is determined for a moment of interest. A MET measure is a normalized measure of energy expenditure, which increases with activity and is non-zero at a moment of interest. For example, a MET measure for an inactive or asleep status or not wearing status is close to 1.0, a MET measure for the user while walking is generally above 2.0, and a MET measure for the user while swimming is between 10.0 and 11.0. While in some embodiments the analyzed sensor information 152 is MET measures, various embodiments use different measures, e.g., motion measures indicative of a motion of the user wearing the wearable electronic device, heart rate measures indicative of the heart rate of the user, etc. The motion measures are sometimes referred to herein as movement measures. Examples of the motion measures include a number of steps taken by the user, a number of floors climbed or descended by the user, etc. In various embodiments, the heart rate sensor, e.g., a heart rate monitor, etc., generates the heart sensor data indicative of a heart rate of the user and calculates the heart rate measures of the user.

The analyzed sensor information 152 for moments of interest is used by the user state tracking unit 190 to generate a state 156 of the user for different periods of time. In some embodiments, each period of time typically includes multiple contiguous moments of interest. In various embodiments, each period of time is as small as one moment of interest. The user state tracking unit 190 includes a user status identifier 120 that classifies each moment 154 of interest into the status of the user based on the analyzed sensor information 152 for that moment of interest. The statuses of the user are classified into the sedentary status and the non-sedentary status, as indicated in the task box 3A.

In some embodiments, the user status classifier 120 classifies the status of the user for the moment 154 of interest as being sedentary, e.g., seated, seated and typing at a computer, typing at a computer, etc., or non-sedentary, e.g., active, running, walking, exercising, dancing, swimming, etc. It should be noted that in various embodiments, when the status of the user is classified as non-sedentary, the user is spending a higher amount of energy compared to energy expended by the user when the status of the user is classified as sedentary. Several methods for classifying the moment 154 of interest are described in more detail below with reference to FIGS. 6A-6B.

In various embodiments, a MET measure is used to determine the non-sedentary status of the user and associates the non-sedentary status with a particular type of activity of the user. For example, according to a MET measure, the user status classifier 120 determines whether the user is running, walking, sprinting, bicycling, swimming, or performing another type of non-sedentary activity.

As described in the task box 3B, a time period detector 122 of the user state tracking unit 190 detects periods of time during which a state of the user is sedentary based on contiguous moments of interest for which the status of the user is classified as sedentary. For example, according to some embodiments described below with reference to FIG. 2, a block of time is determined by the time period detector 122 to have a sedentary state when it is determined by the time period detector 122 that the block of time includes contiguous moments of interest of sedentary statuses.

The state 156 of the user for different periods of time is used by the sedentary notification unit 192 to generate one or more sedentary alerts 158 to notify the user. Examples of the one or more sedentary alerts 158 are provided below. The one or more sedentary alerts 158 encourage the user to limit a length of sedentary time periods. At the task box 4, a sedentary state monitor 124 of the sedentary notification unit 192 generates the one or more sedentary alerts 158, e.g., a notification, etc., for providing to the user to encourage the user to alter his/her sedentary behavior. The one or more sedentary alerts 158 are provided to the user through a user interface 126, which includes a display device of the wearable electronic device. In some embodiments, the user receives the one or more sedentary alerts 158 through a vibration of the wearable electronic device, a message displayed on the display device of the wearable electronic device, and/or a sound emitted by a speaker within the wearable electronic device.

In some embodiments, the sensor data analyzer 112 is located within the wearable electronic device or within one of the other electronic devices. For example, a processor of the wearable electronic device or of one of the other electronic devices performs operations described herein as being performed by the sensor data analyzer 112. In several embodiments, the user status classifier 120 is located within the wearable electronic device or in one of the other electronic devices. For example, the processor of the wearable electronic device or of one of the other electronic devices performs operations described herein as being performed by the user status classifier 120. In various embodiments, the time period detector 122 is located within the wearable electronic device or in one of the other electronic devices. For example, the processor of the wearable electronic device or of one of the other electronic devices performs operations described herein as being performed by the time period detector 122. In several embodiments, the sedentary state monitor 124 is located within the wearable electronic device or in one of the other electronic devices. For example, the processor of the wearable electronic device or of one of the other electronic devices performs operations described herein as being performed by the sedentary state monitor 124. In some embodiments, the user interface 126 is located within the wearable electronic device or in one of the other electronic devices. For example, the processor of the wearable electronic device or of one of the other electronic devices performs operations described herein as being performed by the user interface 126. Examples of a processor include an application specific integrated circuit (ASIC), a programmable logic device (PLD), a central processing unit, a microprocessor, a controller, a microcontroller, etc.

In some embodiments, instead of the processor of the wearable electronic device performing the operations described herein as being performed by the sensor data analyzer 112, the user status classifier 120, the time period detector 122, the sedentary state monitor 124, and the user interface 126, different processors of the wearable electronic device perform the operations. For example, a processor of the wearable electronic device performs an operation described herein as being performed by the sensor data analyzer 112, another processor of the wearable electronic device performs an operation described herein as being performed by the user status classifier 120, yet another processor of the wearable electronic device performs an operation described herein as being performed by the time period detector 122, another processor of the wearable electronic device performs an operation described herein as being performed by the sedentary state monitor 124, and another processor of the wearable electronic device performs an operation described herein as being performed by the user interface 126. Similarly, in various embodiments, instead of the processor of one of the other electronic devices performing the operations described herein as being performed by the sensor data analyzer 112, the user status classifier 120, the time period detector 122, the sedentary state monitor 124, and the user interface 126, different processors of the one of the other electronic devices perform the operations.

In various embodiments, one or more processors of the wearable electronic device perform the operations described herein as being performed by the sensor data analyzer 112, the user status classifier 120, the time period detector 122, the sedentary state monitor 124, and the user interface 126. Similarly, in some embodiments, one or more processors of one of the other electronic devices perform the operations described herein as being performed by the sensor data analyzer 112, the user status classifier 120, the time period detector 122, the sedentary state monitor 124, and the user interface 126.

It should be noted that in embodiments in which tasks described above with reference to task boxes 2 through 4 are performed by the components 112, 120, 122, and 124 located in one of the other electronic devices, the wearable electronic device includes a display device to display the one or more sedentary alerts 158. Moreover, in these embodiments, the wearable electronic device and one of the other electronic devices communicate with each other via a communication medium, e.g., a universal serial bus cable, a wireless protocol air medium, a serial cable, a parallel cable, etc. An example of the wireless protocol includes Bluetooth™.

Figure 1B:
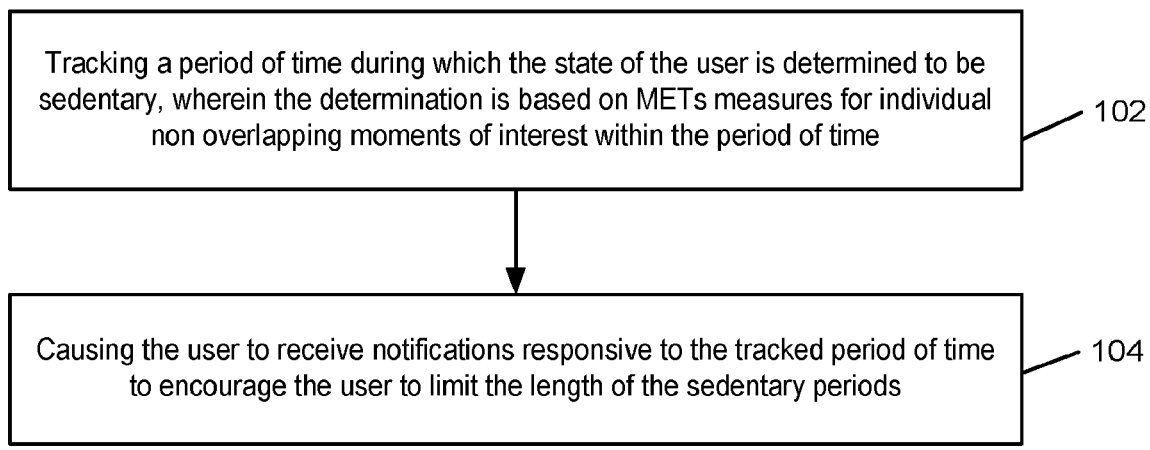
FIG. 1B illustrates a flow diagram of operations for tracking sedentary periods of time and causing a user to receive notifications based on the sedentary periods, according to some embodiments described in the present disclosure.

FIG. 1B illustrates a flow diagram of a method for tracking a sedentary period of time and causing the user to receive notifications based on the sedentary period of time, according to various embodiments described in the present disclosure. At an operation 102 of the method, a period of time during which the state of the user is determined to be sedentary, sometimes referred to herein as the "sedentary period of time", is tracked by the time period detector 122. The determination of the period of time is based on the MET measures for individual non overlapping moments of interest within each period of time. Further, in some embodiments, the MET measures are generated within the wearable electronic device based on the sensor data 150 received from the one or more sensors 110 (FIG. 1A), e.g., a three axis accelerometer and a heart rate sensor, etc. Examples of the MET measures include movement measures calculated based on the sensor data 150 from the motion sensor and heart rate measures calculated based on the sensor data 150 from the heart rate sensor housed within the same wearable electronic device. If a length of the sedentary period of time exceeds a pre-determined threshold time period, it is determined by the time period detector 122 that the state of the user is sedentary.

At an operation 104 of the method for tracking the sedentary period of time, an act of providing the user with notifications to encourage the user to limit a length of the sedentary period of time is performed based on the tracking at the operation 102. In some embodiments, the operation 104 is performed within the wearable electronic device and the user is notified by receiving a message on the display device of the wearable electronic device, a vibration of the wearable electronic device, and/or a sound emitted by speakers of the wearable electronic device.

In some embodiments, a notification, as described herein, is an electronic notification that is sent to a display device. For example, the electronic notification is rendered by a processor to be displayed on a display device. In various embodiments, the electronic notification is provided in the form of a vibration or a sound.

Figure 2:
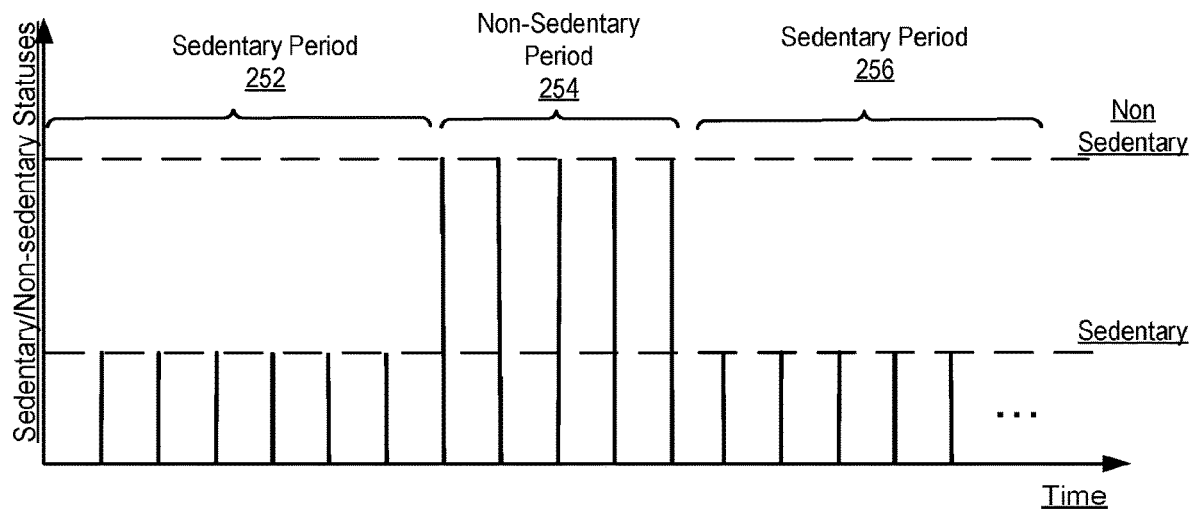
FIG. 2 illustrates a use of sedentary and non-sedentary statuses of the user to determine periods of time in which a state of the user is sedentary, according to several embodiments described in the present disclosure.

FIG. 2 illustrates a use of the user's statuses of sedentary or non-sedentary to determine period of times in which the state of the user is sedentary according to some embodiments described in the present disclosure. As illustrated in FIG. 2, the statuses are illustrated as either sedentary or non-sedentary over time, e.g., at each moment of interest, etc. From the sedentary or non-sedentary statuses, non-overlapping, consecutive periods of time are derived. During each of the consecutive periods of time, the user is in either a sedentary state or a non-sedentary state. Each of the consecutive periods of time span one or more moments of interest. Also, as illustrated in FIG. 2, the consecutive periods of time have different states of the user, and the consecutive periods of time are described by the task box 3B.

Specifically, FIG. 2 shows that the consecutive periods of time are derived: a sedentary period 252, a non-sedentary period 254, and a sedentary period 256, each of which spans multiple contiguous moments of interest for which the status of the user is identical. The sedentary period 252 includes 6 moments of interest each of which has the status classified as sedentary. Comparatively, the non-sedentary period 254 includes 5 moments of interest, each of which has the status classified as non-sedentary. Transitions between the states of the user are represented by edges of the periods of time. e.g., when one time period ends and the next begins, etc., To illustrate, the state of the user transitions from the sedentary state to the non-sedentary state at an end of the sedentary period 252 of time and at a beginning of the non-sedentary period 254 of time.

In some embodiments, the time period detector 122 (FIG. 1A) detects and records alternating periods of time in which the state of the user is sedentary or non-sedentary. For example, the sedentary periods of time 252 and 256, and the non-sedentary period of time 254, illustrated in FIG. 2, are recorded over a span of time, e.g., an hour, a day, a week, etc., to be presented to the user or to perform further analysis with regard to a sedentary behavior of the user. The determined periods of time with the states, e.g., the sedentary state, the non-sedentary state, etc., are presented to the user on the display device of the wearable electronic device or a display device of one of the other electronic devices, e.g., a tablet, a smartphone, a computer, etc., which receives the determined periods of time and the states as data from the wearable electronic device. In some embodiments, the one of the other electronic devices generates the determined periods of time and the states. The user then views his/her sedentary behavior indicated by the determined periods of time and the states, and tracks his/her improvement over time.

In some embodiments, the user shares information about his/her sedentary behavior with friends, colleagues, or teammates via a network, e.g., a social network, etc. The friends, colleagues, or teammates compete with each other based on their respective sedentary states determined by their respective recorded sedentary periods.

In various embodiments, additional sensor data is used to further disambiguate between sedentary periods and other time periods during which the user is asleep and/or not wearing the wearable electronic device. The wearable electronic device is able to detect time periods during which the user is asleep or not wearing the wearable electronic device. For example, the one or more sensors 110 cannot detect information, e.g., the motion sensor data, the heart sensor data, number of steps taken, etc., about the user. To further illustrate, when the wearable electronic device is not being worn by the user, the one or more sensors detect a number of steps taken by the user to be zero for a time period. The time period satisfies the MET measures or motion based criteria for sedentary time, but do not qualify as sedentary because the user is not wearing the wearable electronic device or is asleep as is detected by the one or more sensors 110. MET measures for the time period during which the user is not wearing the wearable electronic device, e.g., while sleeping, while showering, etc., or is asleep are filtered out by the processor of the wearable electronic device or the processor of one of the other electronic devices before or during a time at which a determination of the sedentary and non-sedentary statuses is made.

Embodiments describing the sedentary state monitor follow.

Figure 3:
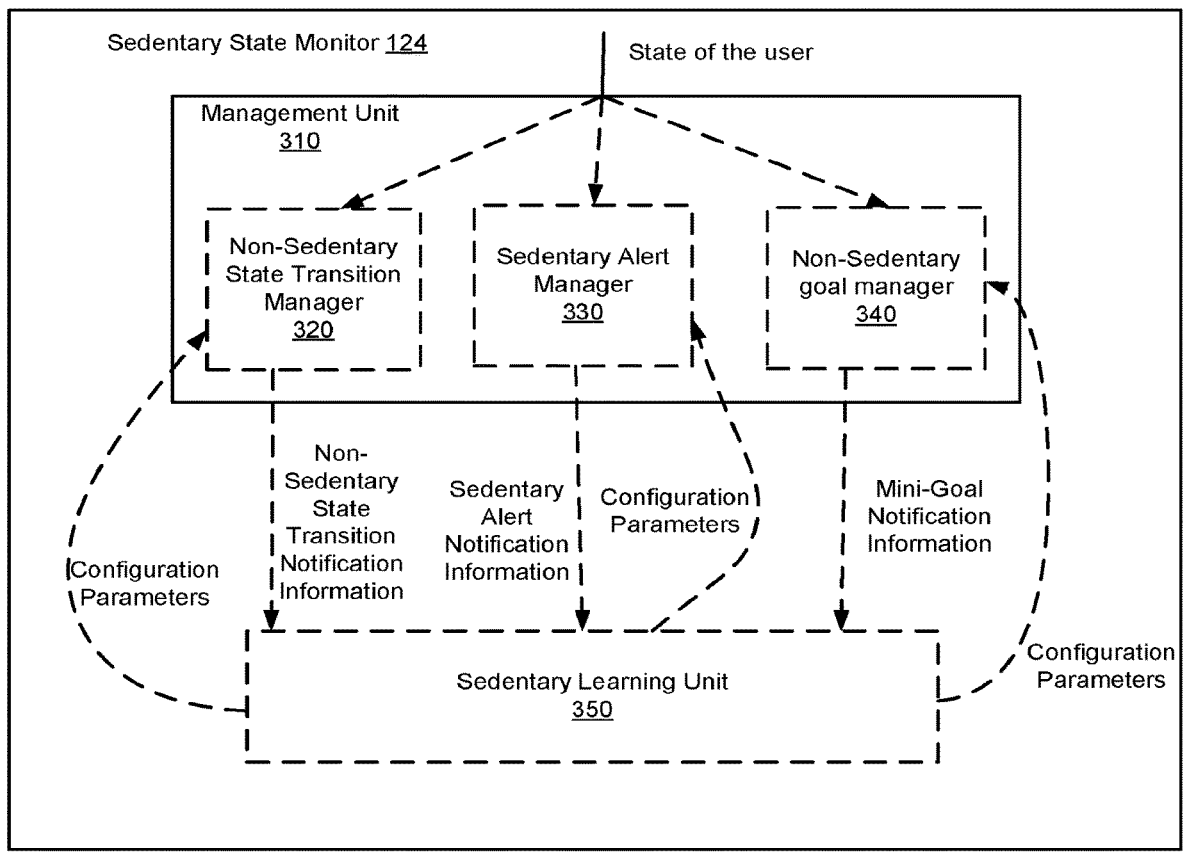
FIG. 3 illustrates a sedentary state monitor for notifying the user based on tracking of the sedentary periods of time to encourage the user to alter his/her sedentary behavior and to limit a length of the sedentary periods, according to some embodiments described in the present disclosure.

Through an automatic detection and tracking of periods of time in which the state of the user is sedentary, the user receives notifications to encourage him/her to alter his/her behavior and be less sedentary. The notifications promote breaking up long periods of sedentary states and decrease an overall time that the user is sedentary. FIG. 3 is a block diagram of an embodiment of the sedentary state monitor 124 for notifying the user based on tracking of sedentary periods of time to encourage the user to alter his/her sedentary behavior and limit a length of the sedentary periods, according to several embodiments described in the present disclosure. The sedentary state monitor 124 includes a management unit 310 that receives the states of the user for periods of time. For example, the state is provided at an end of a period of time after which a preceding state of the user has changed. To illustrate, after a transition between two consecutive states of the user, it is indicated to the management unit 310 that a current period and the user's state has begun. As another example, the states are provided as a current stream of information that includes a transition between two consecutive states. As yet another example, the states are provided in bulk at regular intervals. To illustrate, a current period of time is thus far X time long, and the management unit 310 detects transitions between two consecutive states during X.

While FIG. 3 shows a non-sedentary state transition manager 320 of the management unit 310, a sedentary alert manager 330 of the management unit 310, and a non-sedentary goal manager 340 of the management unit 310, in some embodiments, the management unit 310 has more, less, and/or different types of managers. In embodiments with multiple types of managers, one or some combination of these managers are used at different times to interact with the user, e.g., by sending notifications to the user through the wearable electronic device of the user or through the one of the other electronic devices based on sedentary states of the user to encourage the user to alter or end a sedentary behavior as discussed in more detail below.

Embodiments describing a behavior triggered alert, e.g., a non-sedentary state transition, etc., follow.

In accordance with several embodiments, the user is notified, e.g., via display of a notification, etc., on the wearable electronic device upon detection that the sedentary period of time has ended and the non-sedentary period of time has begun, e.g., the user started moving, etc., and upon determination that the non-sedentary period of time exceeded a threshold period of time. While in some embodiments, the threshold period of time is the same for all types of activities, in various embodiments, the threshold period of time is different for at least certain type of activities. The user receives the notification, e.g., a message displayed on the display device of the wearable electronic device, a vibration of the wearable electronic device, and/or a congratulations sound on the wearable electronic device, etc., that notifies the user that he/she has just ended a sedentary period of time. The notification is intended to encourage the user to keep moving and remain active to limit a total amount of time for which the state of the user is sedentary.

Figure 4:
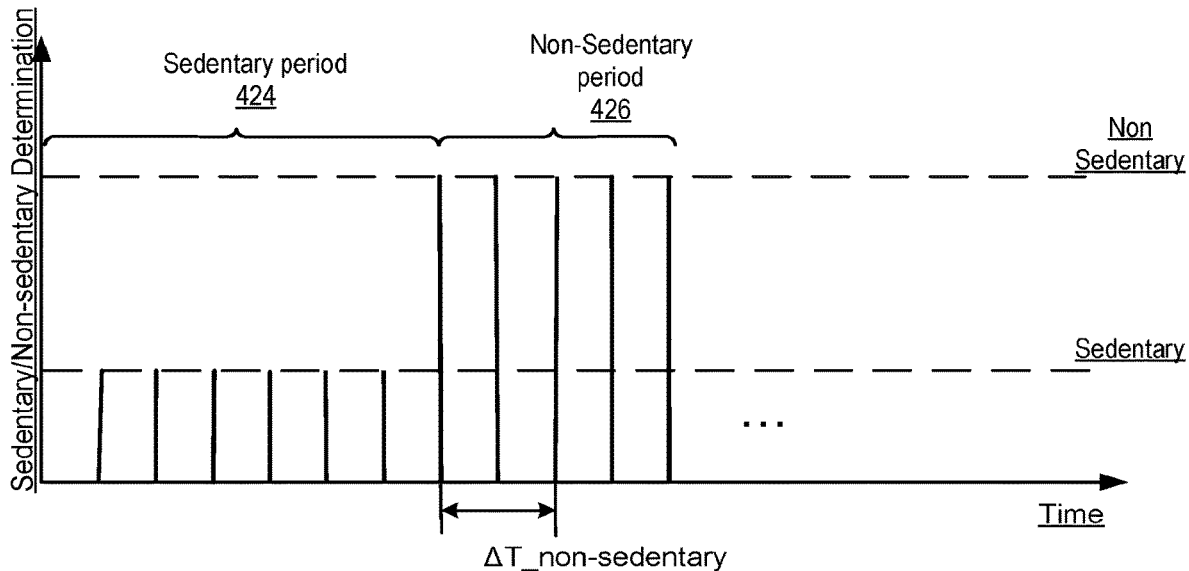
FIG. 4 illustrates a communication of a notification to the user based on a detection of an end of a sedentary period of time and of a beginning of a non-sedentary period of time, which has exceeded a threshold period of time, according to various embodiments described in the present disclosure.

FIG. 4 illustrates a communication of a notification to the user based on a detection of an end of a sedentary period 424 of time and a beginning of a non-sedentary period 426 of time, which has exceeded the threshold period of time, according to some embodiments described in the present disclosure. In some embodiments, the time period detector 122 (FIG. 1A) detects the sedentary period 424 of time of the user and upon detection 412 that the state of the user has changed from sedentary to non-sedentary for the threshold period of time, the time period detector 122 notifies the non-sedentary state transition manager 320 (FIG. 3), which communicates 414 a notification, e.g., non-sedentary state transition notification information, etc., to the wearable electronic device of the user. As an example, it is detected that the state of the user has changed from sedentary to non-sedentary when a set of one or more moments of interest included in the non-sedentary period 426 of time meet the threshold period of time. In some embodiments, the state of the user is detected to be non-sedentary when the user performs one of a variety of activities, e.g., running, sprinting, walking briskly, puttering around, etc., for a period of time, e.g., 30 seconds, 10 seconds, 1 minute, 3 minutes, etc.

In various embodiments, the non-sedentary period 426 of time is determined by the time period detector 122 based on statuses of the user at moments of interest. In some embodiments, an end of the sedentary period 424 of time is detected when a non-sedentary state of the user is detected.

In several embodiments, the non-sedentary state is detected based on a type of activity that the user is performing. For example, when the user runs for 30 seconds, e.g., the status of the user is classified as "non-sedentary, running" for 30 seconds, etc., a change in the state of the user from sedentary to non-sedentary is detected and the user receives a notification. As another example, when the user sprints for at least 10 seconds, e.g., the status of the user is classified as "non-sedentary, sprinting" for at least 10 seconds, etc., a change in the state of the user from sedentary to non-sedentary is detected and the user receives a notification. As yet another example, when the user walks briskly for 1 minute, e.g., the status of the user is classified as "non-sedentary, walking" for 1 minute, etc., a change in the state of the user from sedentary to non-sedentary is detected and the user receives a notification. As still another example, when the user putters around for at least 3 minutes, e.g., the status of the user is classified as "non-sedentary, puttering" for at least 3 minutes, etc., a change in the state of the user from sedentary to non-sedentary is detected and the user receives a notification.

In some embodiments, the time period detector 122 detects the sedentary period 424 of time and upon detection 412, of a non-sedentary moment of interest, e.g., one or more moments of interest included in the non-sedentary period 426 of time, etc., the time period detector 122 notifies the non-sedentary state transition manager 320, which determines that the non-sedentary period of time exceeds the threshold period of time and communicates 414 a notification to the wearable electronic device of the user that the threshold period of time is met. The notification that the threshold period of time is met is indicative that the user has ended the sedentary period 424 of time and is now active. The notification is intended to encourage the user to be more active and break sedentary periods more often.

In various embodiments, the notification that the threshold period of time is met is in the form of a sentence, or a motivational statement, or a positive message displayed on the display device of the wearable device. Examples of a non-exhaustive list of exemplary motivational statements that indicate whether the threshold period of time is met include "good job!," "great work," "keep moving," "keep going"; "don't stop"; "step more"; "xx hours stationary" (where xx is how long the user has been sedentary); "keep walking"; "take a xx minute walk" (where xx is a value between 1-20, for example 2); "you got up after xx hours yy minutes of sitting" (where xx is the number of hours and yy the number of minutes the user is sedentary); "you're at x steps. can you get to x+200?" (where x is the number of steps taken since ending the sedentary period); "take the long way?"; "walking meeting?"; "let's go!"; "Walk to success!"; "Let's call u butter cuz u on a roll!"; "you're on fire!"; "movin' and a groovin'"; "Don't stop movin' ! !"; "grab a friend, keep walking!"; "you can't catch me!"; "Good job, you sat around for x hours and now you finally got up"; "up and at'em"; "walk like you just robbed a bank"; "Staying on top of it!"; "way to go"; "Way to move!"; "Way to work it!"; "you did it!"; "Looking healthy!"; "Good for you :)"; "Great!"; "score!"; and "nice!", etc.

Embodiments describing rolling alerts follow.

In various embodiments, the user is notified through the wearable electronic device upon detection that the user has been sedentary for a threshold amount of time, which is sometimes referred to herein as a threshold sedentary time period. When the user has been sedentary for an extended period of time, a sedentary alert is communicated to the user to inform him/her of the extended period of time and encourage him/her to end the extended period. The sedentary alert is a message displayed on the display device of the wearable electronic device, a sound emitted by the wearable electronic device, and/or a vibration of the wearable electronic device. The sedentary alert is intended to encourage the user to start moving and become active to end the sedentary period.

In some embodiments, the threshold sedentary time period is 1 hour, or 2 hours, or 20 minutes, or 40 minutes, or a few seconds, or a few minutes, or a few hours. In various embodiments, the threshold sedentary time period is configurable, e.g., the user selects a length of a window of sedentary time after which he/she would like to be notified to end the sedentary time. In several embodiments, the threshold sedentary time period is dynamically adjusted, e.g., reduced or increased based on various factors, etc., and/or capable of being automatically disabled and/or manually disabled by the user.

In some embodiments, the user sets preferences for a type of alert to be received. For example the user selects a sound, a particular message to be displayed, and/or a vibration. In various embodiments, the user sets the sedentary state monitor 124 (FIG. 1A) such that sedentary periods of time are monitored within specific intervals of times. For example, the sedentary periods or non-sedentary periods of time are monitored during the day between 8 AM and 8 PM of a day and not monitored for remaining times of the day.

In some embodiments, an input, e.g., one or more preferences, etc., is received from the user via an input device, e.g., a keypad, a touchscreen of the display device, a stylus, etc., of the wearable electronic device or via an input device, e.g., a keypad, a touchscreen of a display device, a stylus, a keyboard, a mouse, etc., of one of the other electronic devices. In embodiments in which the input is received at the wearable electronic device and the sedentary state monitor 124 is located within one of the other electronic devices, the input is communicated from a communication device of the wearable electronic device to a communication device of the one of the other electronic devices. The communication device of the one of the other electronic devices provides the input to the sedentary state monitor 124 of the one of the other electronic devices. Examples of a communication device includes a device that applies a Bluetooth protocol, an Internet Protocol (IP), an Ethernet protocol, a Transmission Control Protocol over IP (TCP/IP) protocol, a Universal Serial Bus protocol, a serial transfer protocol, a parallel transfer protocol, etc. In embodiments in which the input is received at one of the other electronic devices and the sedentary state monitor 124 is located within the wearable electronic device, the input is communicated from the communication device of the one of the other electronic devices to the communication device of the wearable electronic device. The communication device of the wearable electronic device provides the input to the sedentary state monitor 124 of the wearable electronic device.

Figure 5:
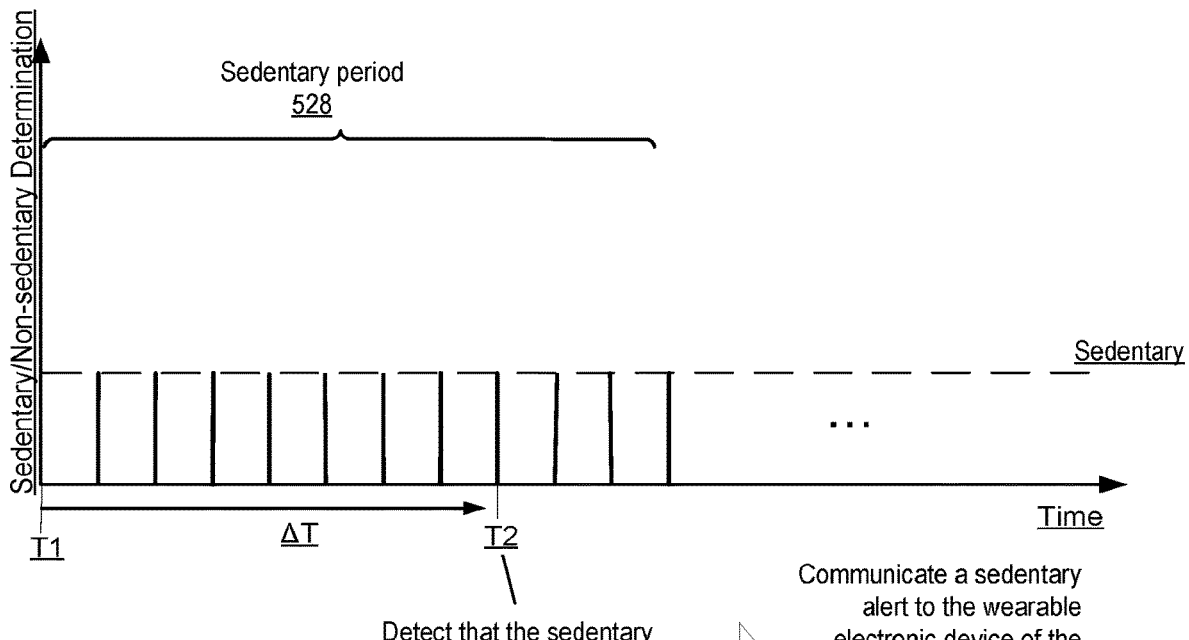
FIG. 5 illustrates a communication of a sedentary alert to the user based on a detection of the sedentary period of time exceeding a sedentary period of time threshold value, according to some embodiments described in the present disclosure.

FIG. 5 illustrates communication of a sedentary alert to the user based on a detection of a sedentary period of time exceeding the threshold sedentary time period, according to various embodiments described in the present disclosure. The time period detector 122 (FIG. 1A) detects 516 a sedentary period 528 of time of the user and upon detection 516 that the sedentary period 528 of time exceeds the threshold sedentary time period $\Delta T$, the sedentary alert manager 330 communicates 518 a sedentary alert, e.g., sedentary alert notification information, etc., to the wearable electronic device of the user. The sedentary alert is indicative that the user has spent more than $\Delta T$ period of time being in the sedentary state and he/she is encouraged to end the sedentary period 528 of time by doing a more active task, e.g., walking, or running, or performing a physical activity with higher energy expenditure than being sedentary, etc. The sedentary alert is intended to inform the user of his/her sedentary behavior and encourage him/her to be more active. In some embodiments, the sedentary alert is in the form of a vibration of the wearable electronic device or a sound emitted by the wearable electronic device through the speaker of the wearable electronic device, a sentence or a message displayed on the display device of the wearable electronic device.

A non-exhaustive list of sedentary alerts includes: "time to get moving!"; "How about a walk?"; "Get moving"; "care for a stroll"; "Move those muscles!"; "Let's move"; "please get up"; "how about a walk?"; "step it up!"; "take a break"; "stretch your legs"; "you were still for xx minutes" (where xx is how long the user has been sedentary); "where you are today is where your mind put you!"; "take care of your body"; "get up!"; "don't just sit there"; "be the example"; "get up, stand up"; "get up, get fit!"; "you've been sitting for 1 hour"; "you know what time it is!"; "woof! let's walk!"; "feed me steps"; "it's never to late to move!"; "time to get steppin'"; "let's move"; "Move! Move! Move!"; "I'm bored. Let's shake it!"; "go get'em!"; "You can do anything you set your mind to"; "Gonna fly now!"; "I dare you to move!"; "More steps please"; "Move your butt"; "UP UP UP"; "Stretcccch"; "Waaalk"; "GETUPANDGO"; "Take a walk"; "Grab a friend, take a walk"; "When the going gets sedentary, the sedentary get going!"; "I believe you can fly!"; "What have you done today to make me feel proud?"; "I want to run"; "Seize the day!"; "Run away!"; "I'm after you!"; "The British are coming"; "Tick tick tick, you're blood sugar is rising"; "Shutup and step"; "Hungry for steps"; "Error: Steps too low"; "Step error"; "Have you forgotten what walking feels like?"; "If you were my Fitbit, I'd walk you"; "it's been a while"; "Time to get up!"; "Get moving"; "Stop being an Eeyore"; "Hop to it"; "Make like a bunny and hop to it"; "It's that time again!"; "Let's go get some water"; "Let's go for a jaunt"; "care for a stroll?";

"stretch them legs!" "streeeeeeaaaaatttccchhh"; "step up 2 the streets"; "now walk it out"; "walk it out"; "left right LEFT!"; and "lets go find some stairs!", etc. In some embodiments, the user alternatively or additionally receives one or more icons, and/or one or more animated images, e.g., animated feet, animated steps, etc., displayed on the display device of the wearable electronic device and the one or more icons and/or the one or more animated images indicate that the user is sedentary for greater than the threshold sedentary time period $\Delta T$.

In various embodiments, upon receipt of the sedentary alert, the user ends the sedentary time period. In several embodiments, upon receipt of the sedentary alert, the user remains sedentary and continues to receive sedentary alerts from the sedentary state monitor 124 at regular time intervals encouraging him/her to move. For example, the user receives sedentary alerts every hour.

In some embodiments, if the user ends the sedentary period 528 of time, the user receives, via the wearable electronic device, a congratulations message from the sedentary state monitor 124, also sometimes referred herein below as a celebration message, to encourage him/her in his/her effort of ending the sedentary period 528 of time as described above. The celebration message is one of celebration messages described further below.

Embodiments describing mini-goal alerts follow.

In some embodiments, the user is encouraged to achieve a mini goal, e.g., 250 steps, or 15 minutes of consecutive non-sedentary moments of interest, etc., during a predetermined window of time. The mini goal is a step towards achieving a predefined goal. The sedentary periods and the non-sedentary activity of the user are tracked by the non-sedentary goal manager 340 (FIG. 3), which interacts with the display device of the wearable device and sends one or more notifications, e.g., mini-goal notification information, etc., to the display device of the wearable device providing information on a progress of the user for reaching the mini goal. For example, the non-sedentary goal manager 340 sends an indication of the progress to notify the user, via a vibration of the wearable electronic device, and/or a message displayed on the display device of the wearable electronic device, and/or a sound emitted by the speaker of the wearable electronic device, of remaining activity to perform to achieve the mini goal before an end of the predetermined window of time. A non-exhaustive exemplary list of notifications and messages that the user receives as part of the mini goal includes "xx MORE STEPS"; "xx STEPS TO GO!"; "xx STEPS LEFT"; "TAKE xx STEPS BEFORE 3 PM"; "xx STEPS TO HOURLY GOAL"; "10 MIN TO GET xx STEPS!"; "xx/yy STEPS DOWN, xx TO GO!"; "every step counts! xx MORE this hour!"; "Only xx steps to go till yy"; and "take xx (animated feet/steps)", where xx is replaced by a number of steps left, and yy is replaced with a total number of steps set to be achieved for the mini-goal.

In some embodiments, instead of receiving an indication of how many steps remain or a length of an activity that remains to achieve the mini goal, the user receives a notification, e.g., a message, mini-goal notification information, etc., via a vibration of the wearable electronic device, and/or a message displayed on the display device of the wearable electronic device, and/or a sound emitted by the speaker of the wearable electronic device, asking him/her to start being active, e.g., walk, run, etc., and later receives a "celebration message" via a vibration of the wearable electronic device, and/or a message displayed on the display device of the wearable electronic device, and/or a sound emitted by the speaker of the wearable electronic device, for achieving the mini goal. For example, the non-sedentary goal manager 340 determines that the mini goal is achieved and provides a notification of achieving the mini goal to the user via a vibration of the wearable electronic device, and/or a message displayed on the display device of the wearable electronic device, and/or a sound emitted by the speaker of the wearable electronic device. The mini goal is sometimes referred to herein as a mini celebration. For example, the mini celebration is "a buzz+smiley", when the user hits yy steps during the predetermined window of time set for the mini goal, e.g., during 1 hour, etc. The buzz is an example of a vibration of the wearable electronic device. In some embodiments, the wearable electronic device includes a tactile feedback device that vibrates to provide a tactile feedback to the user to provide a notification to the user.

While in some embodiments, the predetermined window of time for which the mini goal, e.g., a non-sedentary goal, etc., is to be achieved is 1 hour, in various embodiments a different predetermined time window, e.g., in a range of 10 minutes to 6 hours, or a range of 20 minutes to 3 hours, every 2 hours, etc., is used. In several embodiments, the predetermined window of time for which the mini goal, e.g., a non-sedentary goal, etc., is to be achieved is configurable, e.g., the user selects a length of the predetermined window of time for achieving the mini goal by setting preferences, in a manner described above. In some embodiments, the predetermined window of time for which the mini goal is to be achieved is dynamically adjusted, e.g., reduced or increased based on various factors, etc., by the sedentary state monitor 124. In some embodiments, the predetermined window of time for which the mini goal is to be achieved is capable of being automatically disabled by the sedentary state monitor 124 and/or manually disabled by the user.

In various embodiments, the user further determines preferences regarding timing for receiving notifications and reminders regarding his/her progress towards the mini goal and provides the preferences via the input device of the wearable electronic device or via the input device of one of the other electronic devices to the sedentary state monitor 124. For example, the user desires to receive a notification some minutes prior to the end of the predetermined window of time, e.g., 50 minutes into the hour, etc., before achieving the mini goal. The notification includes information indicating that the mini goal is to be achieved and remaining activities, e.g., a number of non-sedentary minutes, a number of steps, etc., to perform to achieve the mini goal. If the user completes the mini goal before the predetermined window of time ends, the user receives a rewarding message from the sedentary state monitor 124 and receives a prize from the sedentary state monitor 124 for that achievement.

A non-exhaustive exemplary list of celebration messages that the user receives for achieving the mini goal is presented herein: "*"; "great job!"; ":-D :-D :-D"; ":) :) :) :)"; "xx/yy!!!"; "another moving hour!"; "winner"; "winner winner chicken dinner"; "champion! champion!"; "xx down!"; "very good!"; "every extra step matters!"; "you=step machine"; "you=on fire!"; "you=awesome!"; "hourly step champ"; "xx steps isn't even that much"; and "my hero", where xx is replaced by a number of steps completed during the predetermined window of time allocated for that mini-goal, and yy is replaced with a number of steps set to be achieved for the mini goal. Further in some embodiments, the user competes with friends via the social network for most mini goals reached.

In various embodiments, the non-sedentary goal manager 340 tracks and records mini goals set and achieved by the user and presents the mini goals set and/or achieved to the user. The mini goals are presented to the user on the display device of the wearable electronic device or one of the other electronic devices, which receives the mini goals from the wearable electronic device via the communication device of the wearable electronic device and the communication device of the one of the other electronic devices. The user then views his/her sedentary behavior and tracks his/her improvement in achieving the mini-goal over time.

In several embodiments, the sedentary alert manager 330 differs from the non-sedentary goal manager 340 in that the sedentary alert manager 330 works on a current sedentary period of time that started when the state of the user transitioned to sedentary, while the non-sedentary goal manager 340 operates off set time windows irrespective of whether the state is sedentary at a beginning of each time window. As previously discussed, two or more of the managers are used in combination to interact with the user via the sedentary state monitor 124 and the wearable electronic device to alter his/her sedentary behavior.

Embodiments describing learning alerts follow.

In some embodiments, a sedentary learning unit 350 of the sedentary state monitor 124 (FIG. 3), is coupled to the managers 320, 330, and 340, and receives notification information, e.g., one or more notifications, etc., sent to the user via the sedentary state monitor 124 (FIG. 1A) from each one of the managers 320, 330, and 340, and determines which of the one or more notifications had an effect of modifying a sedentary behavior of the user. For example, the sedentary learning unit 350 determines which of the one or more notifications succeeded in altering general sedentary behavior of the user by limiting a length of the sedentary period of time.

While in some embodiments, each of the managers 320, 330, and 340 transmits the notification information regarding a time at which the one or more notifications, e.g., the non-sedentary state transition notification information, the sedentary alert notification information, and the mini-goal notification information, etc., is sent, in various embodiments, the managers 320, 330, and 340 transmit more, less, or different data as part of the notification information. For example, the managers 320, 330, and 340 transmit a type of notification, e.g., a message, a vibration, and/or a sound, to the sedentary learning unit 350. As another example, the managers 320, 330, and 340 transmit information regarding a result of a notification sent to the user, e.g., whether the user ended his/her sedentary period, etc. to the sedentary learning unit 350.

In some embodiments, the sedentary learning unit 350 receives the sensor data 150 (FIG. 1A) from the one or more sensors 110 (FIG. 1A) to determine whether a transmitted notification had an effect of modifying a sedentary behavior of the user. The sedentary learning unit 350 records the sensor data 150 over a period of time to learn which type of notification, e.g., personality or tone of a message, etc., and which context, e.g., a time, a location, etc., has a desired effect on the user. Examples of the desired effect include a decrease in long periods of sedentary time, a decrease in a number of the sedentary states over time, a decrease in a number of sedentary statuses over time, etc. The sedentary learning unit 350 determines improved preferences and settings, e.g., configuration parameters, etc., for configuring at least one of the managers 320, 330, and 340 based on the notification information received.

The sedentary learning unit 350 learns a behavior of the user in response to the notifications from the managers 320, 330, and 340 and reacts to the user's behavior to improve the user's response to the notifications. For example, the sedentary learning unit 350 changes a configuration of one of the managers 320, 330, and 340, e.g., by transmitting configuration parameters to that manager, etc., to change to a time of day when the user might respond to a notification when the sedentary learning unit 350 determines that at another particular time of a day, the user never responds to the notification. As another example, the sedentary learning unit 350 changes a configuration of the sedentary alert manager 330 by modifying a length of the threshold sedentary period after which a notification is sent to the user. As yet another example, the sedentary learning unit 350 modifies a type of notification sent to the user, e.g., configures one of the managers 320, 330, or 340 to send a message to be displayed on the display device of the wearable electronic device instead of a vibration alert, e.g., a buzz, etc., or to cause an emission of a sound by the speakers of the wearable electronic device instead of a vibration, or to change the sound emitted, or to change the tone of a message, or to modify the type of notification.

In some embodiments, the sedentary learning unit 350 changes a plurality of configuration parameters such that one of the managers 320, 330, and 340 operates at a given time of the day. For example, the sedentary learning unit 350 determines that between certain hours of the day, e.g., 8 AM to 12 PM, etc., the user's response to notifications received from the non-sedentary state transition manager 320 is better than the user's response to notifications received from the sedentary alert manager 330. In this example, the sedentary learning unit 350 determines configuration parameters that disable a use of the sedentary alert manager 330 during those hours, e.g., 8 AM to 12 PM, etc. While the sedentary alert manager 330 and the non-sedentary state transition manager 320 are described in this example, in various embodiments, the sedentary learning unit 350 determines configuration parameters to disable or enable another manager, e.g., the non-sedentary goal manager 340, etc., and/or determines other hours of day during which to configure the managers 320, 330, or 340. While in several embodiments, the sedentary learning unit 350 changes a configuration of at least one of the managers 320, 330, and 340, in some embodiments, the sedentary learning unit 350 transmits a recommendation of a configuration of at least one of the managers 320, 330, and 340 to the display device of the wearable electronic device to be approved by the user prior to the configuration of the at least one of the managers 320, 330, and 340 with the changed configuration parameters.

In various embodiments, the sedentary learning unit 350 allows the user to snooze the sedentary alert notification information, such that the wearable electronic device reminds the user at a later time to perform a non-sedentary activity. The sedentary learning unit 350 records data related to an act, performed by the user via the input device of the wearable electronic device or the input device of one of the other electronic devices, of snoozing the sedentary alert notification information. For example, the data related to the act of snoozing includes a type of notification snoozed, a time at which the notification is snoozed, the state, e.g., sedentary, non-sedentary, etc., of the user at that time, a geographical location at which the notification is snoozed, etc. The sedentary learning unit 350 uses the data related to the act to change a configuration of one or more of the managers 320, 330, and 340. For example, if the user snoozes one or more of the managers 320, 330, and 340 at a particular time of a day, a configuration is changed in the manager to avoid operating during that time. This is used to improve the user's experience and instill greater confidence in the wearable electronic device. In some embodiments, the sedentary learning unit 350 is implemented using one or more of the following: a decision tree, a random forest, a support vector machine, a neural network, a K-nearest neighbor, a Naïve Bayes, and Hidden Markov Models.

In various embodiments, the user is able to set preferences for a type of notification received based on his/her sedentary behavior. For example, the user is able to select a subset of subunits, e.g., the non-sedentary state transition manager 320, the sedentary alert manager 330, the non-sedentary goal manager 340, etc., of the sedentary state monitor 124 via the input device of the wearable electronic device or the input device of one of the other electronic devices for use in notifying the user based on his/her sedentary behavior. Furthermore, the user is able to select a sound, a particular message to be displayed on the display device of the wearable electronic device, and a vibration for each type of message received on the wearable electronic device. The user chooses a combination of the types of notifications to be received simultaneously. The user sets the sedentary state monitor 124 via the input device of the wearable electronic device or the input device of one of the other electronic devices such that the sedentary periods are monitored within specific intervals of times. For example, the user desires to monitor the sedentary periods or the non-sedentary periods during a day between 8 AM and 8 PM.

Embodiments describing a classification of the status of the user based on the MET measures follow.

In some embodiments, the MET measures are used to determine the sedentary status or the non-sedentary status of the user. Thus, the MET measures are sometimes referred to as sedentary coefficients. The user status classifier 120 (FIG. 1A) receives a MET measure for a moment of interest and determines whether the MET measure is below a predetermined threshold. When the MET measure is below the predetermined threshold, the status of the user for that moment of interest is classified as being the sedentary status by the user status classifier 120. When the MET measure is above the predetermined threshold, the status of the user is classified as being non-sedentary for that moment of interest by the user status classifier 120 and the user is determined to be active by the user status classifier 120.

Figure 6A:
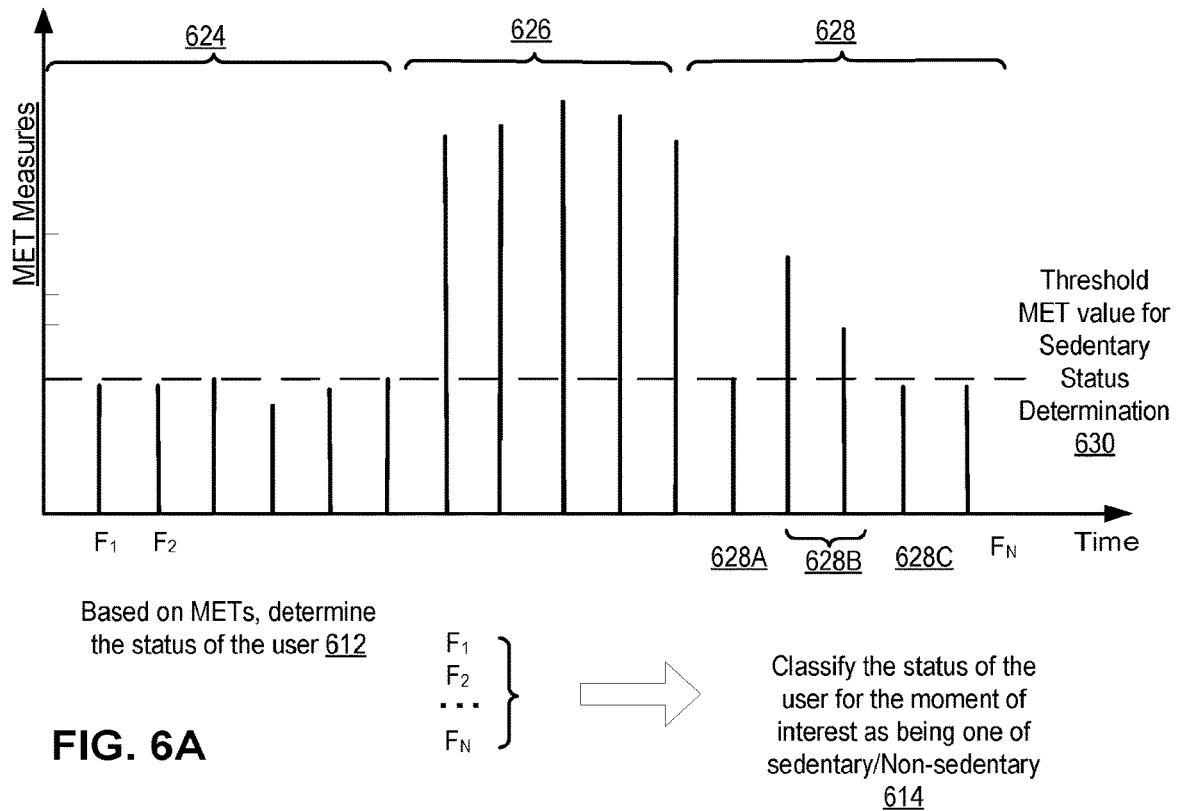
FIG. 6A illustrates a recordation of metabolic equivalent of task (MET) measures at consecutive moments of interest over a period of time and a classification of a status of the user at each moment of interest based on the MET measures, in accordance with various embodiments described in the present disclosure.

FIG. 6A illustrates a recordation of the MET measures at consecutive moments of interest over a period of time and a classification of a status 612 of the user by the user status classifier 120 (FIG. 1A) at each moment of interest based on the MET measures, in accordance some embodiments described in the present disclosure. The status 612 of the user is classified 614 as being non-sedentary by the user status classifier 120 at a moment of interest based on a MET measure exceeding a threshold MET value at that moment of interest, according to several embodiments described in the present disclosure. The MET measures are generated by the sensor data analyzer 112 (FIG. 1A) for a number of moments of interest, e.g., $F_1, F_2 \ldots F_N$, etc., and each MET measure, e.g., MET value, etc., is compared by the user status classifier 120 with the threshold MET value used for determination 630 of the sedentary status. MET measures 624 are all below the threshold MET value as determined by the user status classifier 120, and each moment of interest for the MET measures 624 is classified 614 and recorded as having the sedentary status by the user status classifier 120 within a memory device, e.g., the computer-readable media, etc., of the wearable electronic device or of one of the other electronic devices. Comparatively, MET measures 626 all exceed the threshold MET value as determined by the user status classifier 120, and each moment of interest for the MET measures 626 is recorded by the user status classifier 120 within the memory device as having the non-sedentary status. MET measures 628 are associated with sedentary and non-sedentary moments of interest by the user status classifier 120. For example, two of the MET measures 628 are above the threshold MET value as determined by the user status classifier 120, and each moment of interest 628B for the two of the MET measures 628 is identified as having the non-sedentary status by the user status classifier 120. The two other illustrated MET values of the MET measures 628 are below the threshold MET value as determined by the user status classifier 120. Each moment of interest 628A and 628C for the two other MET values is identified as having the sedentary status by the user status classifier 120. In some embodiments, the threshold MET value is within the range of 0.8-1.8 MET, e.g., 1.5 MET, etc. The classification 614 of the moments of interest illustrated at FIG. 6A yields sedentary and non-sedentary moments of interests illustrated in FIG. 2.

Figure 6B:
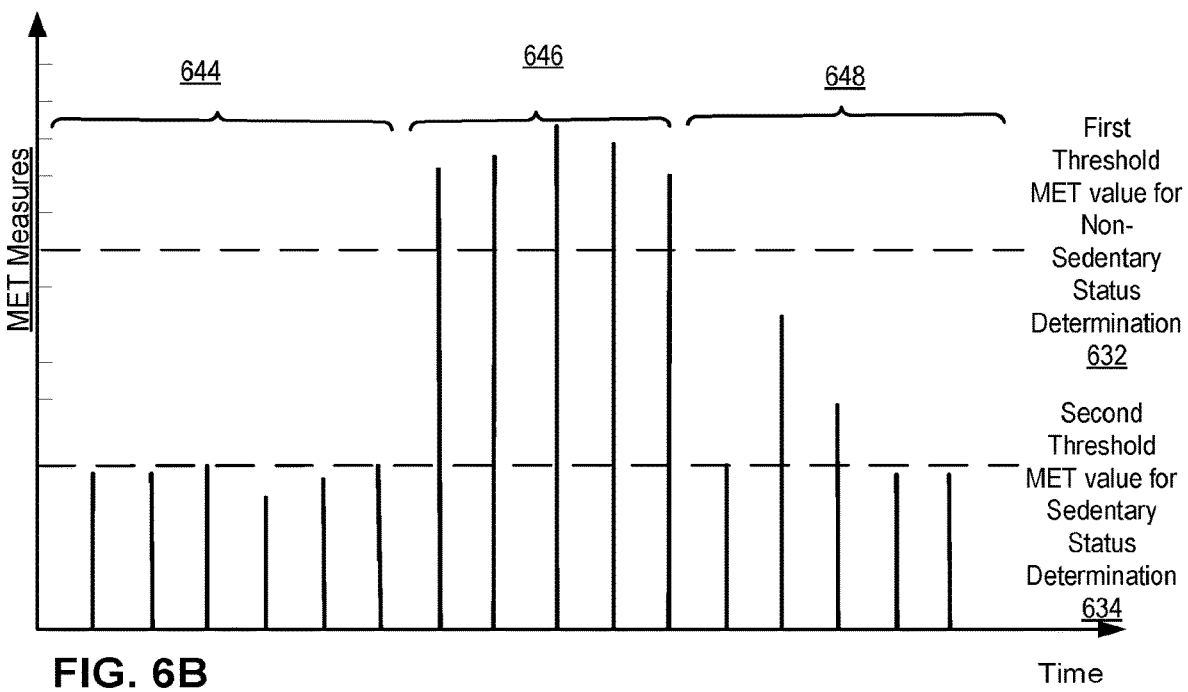
FIG. 6B illustrates a recordation of the MET measures at consecutive moments of interest over a period of time and the classification of the status of the user at each moment of interest based on the MET measures, in accordance with some embodiments described in the present disclosure.

FIG. 6B illustrates a recordation of the MET measures at consecutive moments of interest over a period of time and a classification of the status of the user by the user status classifier 120 (FIG. 1A) at each moment of interest based on the MET measures, in accordance with various embodiments described in the present disclosure. The status of the user is classified as being non-sedentary at a moment of interest based on a MET measure exceeding a first threshold MET value at that moment of interest. The status of the user is classified as being sedentary at a moment of interest based on a MET measure being below a second threshold MET value at that moment of interest. In addition, the status of the user is classified as being sedentary at a moment of interest if the MET value exceeds the second threshold MET value, is below the first threshold MET value, and it is further preceded and followed by a moment of interest with a sedentary status. In some embodiments, a group of N consecutive moments are classified as having sedentary status if a MET measure associated with each moment is between the first and the second threshold MET values and the group of N consecutive moments of interest is immediately preceded and succeeded by a moment of interest with a sedentary status. Examples of N consecutive moments of interest include moments of interest, each occurring at 1 minute time intervals (e.g., where N is between 1 and 5), or each occurring at time intervals between 1 minute and 5 minutes, or each having 1 second time intervals (e.g., where N is between 1 and 300), or each occurring at time intervals between 1 second and 300 seconds, etc. If the N moments of interest occur at longer time intervals, e.g., every 10 minutes, etc., then N is smaller, e.g., 2, etc. In the embodiments discussed above, the second threshold MET value is lower than the first threshold MET value.

Each of the MET measures generated by the sensor data analyzer 112 is compared by the user status classifier 120 with the first threshold MET value used for recording a non-sedentary status 632 and with the second threshold MET value used for recording a sedentary status 634. The recordation of the non-sedentary status 632 and the sedentary status 634 in the memory device is performed by the user status classifier 120. MET measures 646 are all above the first threshold MET value, and each moment of interest for the MET measures 646 as determined by the user status classifier 120 to have the non-sedentary status is recorded by the user status classifier 120. The MET measures 644 are all below the second threshold MET value as determined by the user status classifier 120, and each moment of interest for the MET measures 644 is recorded by the user status classifier 120 as having the sedentary status. Comparatively, some of MET measures 648 exceed the second threshold MET value but are below the first threshold MET value as determined by the user status classifier 120, while other ones of the MET measures 648 are below the second threshold MET value as determined by the user status classifier 120. A first moment of interest of a group of contiguous moments of interest for the MET measures 648 has a MET value below the second MET threshold value as determined by the user status classifier 120, while a second moment of interest and a third moment of interest for the MET measures 648 has a MET value between the first and the second threshold MET values as determined by the user status classifier 120, immediately followed by moments of interest with a MET value below the second threshold MET value. In this example, all moments of interest for the MET measures 648 are determined by the user status classifier 120 as having the sedentary status despite having two moments within the contiguous group of moments with MET measures exceeding the second threshold MET value.

As described above, in some embodiments, a MET measure determines the non-sedentary status of the user associated with a particular type of activity of the user. For example, according to a MET measure, the user status classifier 120 determines whether the user is running, walking, sprinting, bicycling, swimming or performing another type of non-sedentary activity. To further illustrate, if a MET measure is within a range of 2.5 to 3.2, a status of the user is classified as "non-sedentary, bicycling". As another example, if a MET measure is within a range of 3.2 to 3.8, a status of the user is classified as "non-sedentary, walking". As yet another example, is a MET measure is between 6.7 to 7.3, e.g., e.g., 7.0, etc., a status of the user is classified as "non-sedentary, jogging".

Embodiments describing a classification based on other sensor information follow.

In some embodiments, the sedentary status of the user for a moment of interest is determined by the user status classifier 120 based on the sensor data 150 (FIG. 1A), e.g., the motion sensor data and/or the biometric data, etc., received from the one or more sensors 110 (FIG. 1A) without the generation of the MET measures. For example, the sedentary status of the user is determined based on the motion measures, e.g., also sometimes referred to as movement measures, etc., and/or the heart rate measures without calculation of MET measures. Some embodiments of a classification of a status of the user at a moment of interest are described in U.S. Pat. No. 8,548,770 "Portable monitoring devices and methods of operating same," which is incorporated by reference herein in its entirety.

Description of exemplary devices with automatic detection of the user's sedentary state or the non-sedentary state and providing notification to the user based on the sedentary state follow.

Figure 7:
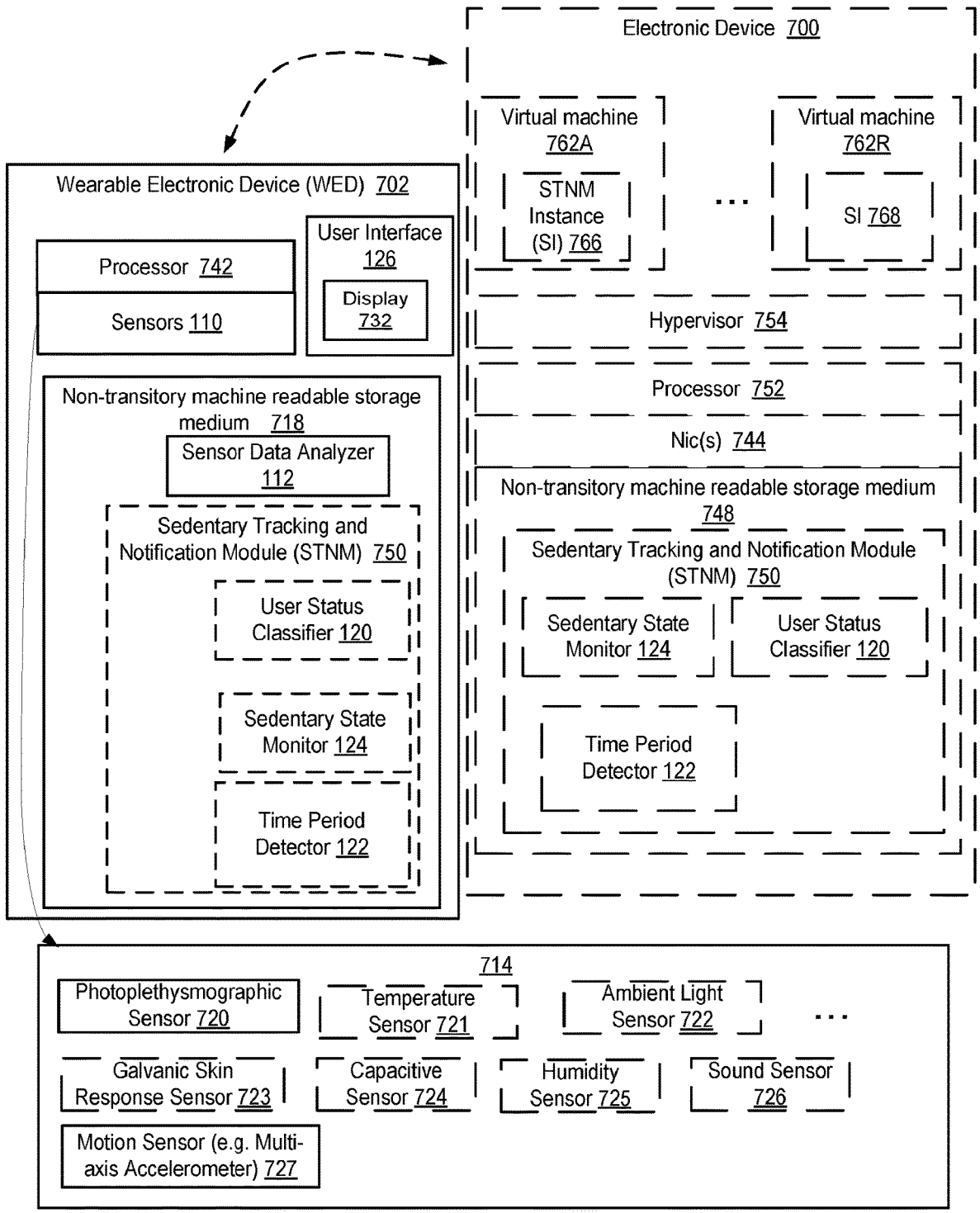
FIG. 7 is a block diagram illustrating a wearable electronic device and an electronic device implementing operations disclosed herein, according to various embodiments described in the present disclosure.

As previously described, while in some embodiments, one or more of the operations, described above, are implemented in the wearable electronic device, in various embodiments, one or more the operations are distributed among electronic devices, e.g., the wearable electronic device and the other electronic devices, etc. FIG. 7 illustrates examples of one such distribution. FIG. 7 is a block diagram illustrating a wearable electronic device 702 and an electronic device 700 implementing operations disclosed according to various embodiments described in the present disclosure. The electronic device 700 is an example of one of the other electronic devices. The wearable electronic device 702 includes a processor 742 and the one or more sensors 110. In some embodiments, instead of the processor 742, multiple processors are used in the wearable electronic device 702.

In some embodiments, the one or more sensors 110 include the motion sensor 727, examples of which include a multi-axis accelerometer, a gyroscope, a gravity sensor, a rotation vector sensor, and a magnetometer. Moreover, in various embodiments, the one or more sensors 110 include one of more other sensors 714, which include a photoplethysmographic sensor 720. In several embodiments, the one or more other sensors 714 include a temperature sensor 721, an ambient light sensor 722, a galvanic skin response sensor 723, a capacitive sensor 724, a humidity sensor 725, and a sound sensor 726.

The wearable electronic device 702 also includes a non-transitory machine readable storage medium 718, which contains the sensor data analyzer 112 as discussed herein above. When executed by the processor 742, the sensor data analyzer 112 causes the wearable electronic device 702 to generate the analyzed sensor information 152 for moments of interest. The wearable electronic device 702 performs functionalities relating to the user status classifier 120, the time period detector 122, and/or the sedentary state monitor 124, some or all of which are included in a sedentary tracking and notification module (STNM) 750, which is stored in the non-transitory machine readable storage medium 718. When executed by processor 742, the STNM 750 causes the wearable electronic device 702 to perform corresponding operations discussed herein above. The wearable electronic device 702 further includes the user interface 126 having a display device 732. Examples of a display device includes a liquid crystal display (LCD) display device, a light emitting diode (LED) display device, a plasma display device, etc. In some embodiments, the user interface 126 includes a speaker, a haptic screen, and/or a vibration mechanism, e.g., a haptic communication device, a rumble pack, a kinesthetic communication device, etc., to allow communication and interaction with the user wearing the wearable electronic device 702.

In some embodiments, the one or more other sensors 714 are not placed within the wearable electronic device 702. The one or more other sensors 714 are distributed around the user. For example, the one or more other sensors 714 are placed on a chest of the user, or a mattress on which the user lies, or a bedside table located by the user, while the wearable electronic device 702 is worn by the user.

FIG. 7 also includes an embodiment of the electronic device 700, e.g., the server including hardware and software, a tablet, a smartphone, etc., containing an application. In some embodiments, the electronic device 700 performs functionalities relating to the user status classifier 120, the time period detector 122, and/or the sedentary state monitor 124, some or all of which are included in the STNM 750, which is stored in a non-transitory machine readable storage medium 748 of the electronic device 700. For example, the STNM 750, instead of being stored in the non-transitory machine readable storage medium 718 of the wearable electronic device 702, is stored in the non-transitory machine readable storage medium 748 of the electronic device 700 for execution by a processor 752 of the electronic device 700. In some embodiments, the sensor data analyzer 112 is stored in the non-transitory machine readable storage medium 748 instead of being stored in the non-transitory machine readable storage medium 718, and is executed by the processor 752.

When executed by processor 752, the STNM 750 causes the electronic device 700 to perform corresponding operations discussed herein above. In some embodiments, the electronic device 700 contains virtual machines (VMs) 762A to 762R, each of which executes a software instance 766 or a software instance 768 of the STNM 950. A hypervisor 754 presents a virtual operating platform for the virtual machines 762A to 762R.

The wearable electronic device 702 collects one or more types of the sensor data 150, e.g., biometric data, etc., from the one or more sensors 110 and/or external devices, and then utilizes the sensor data 150 in a variety of ways. Examples of the biometric data include data pertaining to physical characteristics of a human body, such as, for example, a heartbeat, a heart rate, perspiration levels, etc. Other examples of the sensor data 150 include data relating to a physical interaction of the human body with an environment, such as accelerometer readings, gyroscope readings, etc. An example of the external devices includes an external heart rate sensor or monitor, e.g., a chest-strap heart rate sensor or monitor, etc. Examples of utilizing the sensor data 150 in the variety of ways include making calculations based on the sensor data 150, storing the sensor data 150, storing the calculations in the non-transitory machine readable storage media 718, automatically acting on the sensor data 150, automatically acting on the calculations, communicating the sensor data 150 to a communication device, such as, one or more network interface controllers 744, etc., of the electronic device 700 over the computer network, such as, for example, the Internet, a wide-area network, a local area network, etc., and communicating the calculations to the communication device over the computer network. Examples of automatically acting on the calculations include an automatic watch check and dismissal gesture detection. As described herein, the wearable electronic device 702 also receives data, e.g., notifications, etc. from one of the other electronic devices for storage and/or display on the display device 732.

In some embodiments, the electronic device 700 includes a display device for presenting any notifications described herein, e.g., the non-sedentary state transition notification information, the sedentary alert notification information, and the mini-goal notification information, etc., which are received from the wearable electronic device 702. For example, the sedentary state monitor 124 of the wearable electronic device 702 generates a notification and sends the notification via a communication device of the wearable electronic device 702 and a communication device of the electronic device 700 to the display device of the electronic device 700 for display on the display device 700.

In various embodiments, the sensor data 150 is obtained by the wearable electronic device 702 and send via the communication device of the wearable electronic device 702 and the communication device of the electronic device 700 to the STNM 750 of the electronic device 700 for performing the operations described herein.

In several embodiments, a notification is generated by the electronic device 700 and is sent from the one or more network interface controllers 744 to the communication device of the wearable electronic device 702 via the computer network for display of the notification on the display device 732. In various embodiments, the sedentary state monitor 124 of the electronic device 700 generates a notification and sends the notification via a communication device of the electronic device 700 and a communication device of the wearable electronic device 702 to the display device 732 for display on the display device 732.

Figure 8:
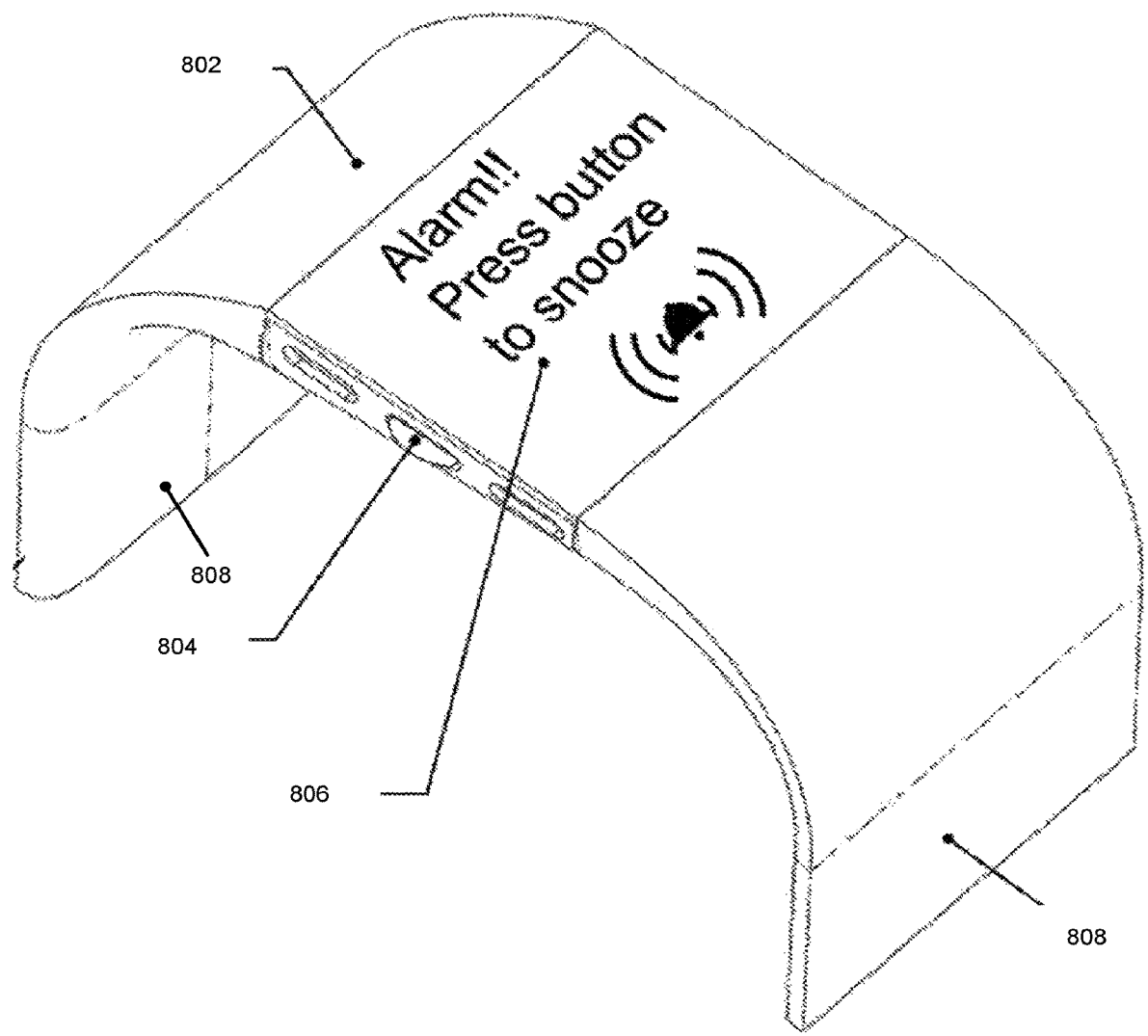
FIG. 8 is a block diagram of a wrist-mounted electronic device having a button, a display, and a wrist band to secure the wrist-mounted electronic device to a forearm of the user, according to some embodiments described in the present disclosure.

FIG. 8 is a block diagram of an embodiment of a wrist-mounted electronic device having a button, a display, and a wrist band to secure the wrist-mounted electronic device to a user's forearm, according to several embodiments described in the present disclosure. For example, FIG. 8 depicts the wearable electronic device 702, such as illustrated in FIG. 7, and that is worn on the user's forearm, like a wristwatch. In FIG. 8, the wrist-mounted electronic device has a housing 802 that contains electronics, e.g., components illustrated in FIG. 7, etc., associated with the wrist-mounted electronic device, a button 804, and a display screen 806 accessible or visible through the housing 802. The display screen 806 is of the display device 732 (FIG. 7). A wristband 808 is integrated with the housing 802.

In some embodiments, the wrist-mounted electronic device incorporates one or more user interfaces including, but not limited to, visual, auditory, touch/vibration, or combinations thereof. In some embodiments, the wrist-mounted electronic device provides haptic feedback through, for instance, a vibration of a motor. In some implementations, the one or more sensors 110 (FIG. 1A) are used as part of the one or more user interfaces, e.g., accelerometer sensors are used to detect when the user taps the housing 802 of the wrist-mounted electronic device with a finger or other object and then interprets such data as a user input for purposes of controlling the wrist-mounted electronic device. For example, double-tapping of the housing 802 of the wrist-mounted electronic device is recognized by the wrist-mounted electronic device as a user input.

While FIG. 8 illustrates an implementation of the wrist-mounted electronic device, in some embodiments, the wrist-mounted electronic device has other shapes and sizes adapted for coupling to, e.g., secured to, worn, borne by, etc., a body or clothing of the user. For example, the wrist-mounted electronic device is designed such that it is inserted into, and removed from, a plurality of compatible cases or housings or holders, e.g., a wristband that is worn on the user's forearm or a belt clip case that is attached to the user's clothing. As used herein, the term "wristband" refers to a band that is designed to fully or partially encircle the user's forearm near a wrist joint. The band is continuous, e.g., without any breaks, or is discontinuous, or is simply open. An example of the continuous band includes a band that stretches to fit over the user's hand or has an expanding portion similar to a dress watchband. An example of the discontinuous band includes a band having a clasp or other connection allowing the band to be closed, similar to a watchband. An example of the open band is one having a C-shape that clasps the user's wrist.

It should be noted that in some embodiments, information, e.g., notifications, etc., are accessed by the user after logging into a user account. For example, the user provides his/her user information, e.g., user name, password, etc., and when the user information is authenticated by the server, the user logs into the user account. In these embodiments, the notifications are posted within the user account. The user account is stored on the server.

In some embodiments, the user accesses the user account to view graphs illustrated in FIGS. 2, 4, 5, 6A, and 6B. The graphs are viewed on the display device of the wearable electronic device or on the display device on one of the other electronic devices.

Some embodiments of the wearable electronic device and of one of the other electronic devices are described in application Ser. No. 15/048,965, filed on Feb. 19, 2016 and titled "Generation of Sedentary Time Information by Activity Tracking Device", in application Ser. No. 15/048,972, filed on Feb. 19, 2016 and titled "Temporary Suspension of Inactivity Alerts in Activity Tracking Device", in application Ser. No. 15/048,976, filed on Feb. 19, 2016 and titled "Live Presentation of Detailed Activity Captured by Activity Tracking Device", and in application Ser. No. 15/048,980, filed on Feb. 19, 2016 and titled "Periodic Inactivity Alerts and Achievement Messages", all of which are incorporated by reference herein in their entirety.

It should be noted that in an embodiment, one or more features from any embodiment described herein are combined with one or more features of any other embodiment described herein without departing from a scope of various embodiments described in the present disclosure.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. An electronic device, comprising:
a communication device configured to communicate with a wearable device including one or more biometric sensors configured to generate samples of motion measures of a user wearing the wearable device for a plurality of moments of interest;
at least one processor; and
a memory storing computer-executable instructions for controlling the at least one processor to:
receive, via the communication device, the samples of the motion measures,
compare the samples of the motion measures for each of the plurality of moments of interest to a first predetermined threshold,
classify the samples of the motion measures for each of the plurality of moments of interest into at least a sedentary status or a non-sedentary status based on the comparison,
determine a first time period for which a defined number of consecutive samples have been classified into the sedentary status,
classify the first time period as having a sedentary state in response to determining that the first time period is greater than a first threshold time period;
send an indication to the wearable device that the first time period is classified as having a sedentary state, wherein the wearable device is configured to present a notification in response to the indication;
determine, based on the samples of the motion measures, that a second time period following presentation of the notification is classified as having the sedentary state; and
send instructions to the wearable device via the communication device to not present subsequent notifications responsive to further indications of time periods that have been classified as having the sedentary state.

2. The electronic device of claim 1, wherein the memory further stores computer-executable instructions for controlling the at least one processor to:
send to the wearable device via the communication device the notification for presentation by the wearable device, and
wherein the notification includes a message recommending ending of the sedentary state.

3. The electronic device of claim 1, wherein the memory further stores computer-executable instructions for controlling the at least one processor to:
detect a third time period for which a number of consecutive samples have been classified into the non-sedentary status,
determine that the third time period is greater than a second threshold time period, and
classify the third time period as having a non-sedentary state upon determining that the third time period is greater than the second threshold time period.

4. The electronic device of claim 3, wherein the memory further stores computer-executable instructions for controlling the at least one processor to:
determine that the third time period is contiguous with a time period that has been classified as having the sedentary state,
identify a transition from the sedentary state to the non-sedentary state upon determining that the third time period is contiguous with the time period that has been classified as having the sedentary state, and
send to the wearable device via the communication device a second notification including a motivational message for display via the wearable device upon identifying the transition from the sedentary state to the non-sedentary state.

5. The electronic device of claim 1, wherein the memory further stores computer-executable instructions for controlling the at least one processor to:
determine that values of the samples of the motion measures for a group of consecutive moments of interest are each greater than the first predetermined threshold and each less than a second predetermined threshold, the second predetermined threshold being higher than the first predetermined threshold,
determine that a value of one of the samples of the motion measures for a moment of interest preceding the group of consecutive moments of interest is classified as having the sedentary status,
determine that a value of one of the samples of the motion measures for a moment of interest subsequent to the group of consecutive moments of interest is classified as having the sedentary status, and
classify each of the samples of the motion measures for the group of consecutive moments of interest as having the sedentary status.

6. The electronic device of claim 5, wherein the memory further stores computer-executable instructions for controlling the at least one processor to:
determine that a size of the group of consecutive moments of interest is less than a size threshold prior to the classifying each of the samples of the motion measures for the group of consecutive moments of interest as having the sedentary status.

7. The electronic device of claim 5, wherein each of the samples of the motion measures is classified as having the sedentary status, the non-sedentary status, or an asleep status.

8. The electronic device of claim 1, wherein the samples of the motion measures comprises at least one of a number of steps taken by the user or a number of floors climbed or descended by the user.

9. A method, comprising:
receiving, via a communication device, a plurality of samples of motion measures for a plurality of moments of interest from a wearable device, the wearable device comprising one or more biometric sensors configured to generate the samples of the motion measures;

comparing, via a processor, the samples of the motion measures for each of the moments of interest to a first predetermined threshold;

classifying the samples of the motion measures for each of the moments of interest into at least a sedentary status or a non-sedentary status based on the comparison of the samples of the motion measures;

determining a first time period for which a defined number of consecutive samples have been classified into the sedentary status;

classifying the first time period as having a sedentary state in response to determining that the first time period is greater than a first threshold time period;

sending an indication to the wearable device that the first time period is classified as having the sedentary state, wherein the wearable device is configured to present a notification in response to the indication;

determining, based on the samples of the motion measures, that a second time period following presentation of the notification is classified as having the sedentary state; and sending instructions to the wearable device via the communication device to not present subsequent notifications responsive to further indications of time periods that have been classified as having the sedentary state.

10. The method of claim 9, further comprising:
sending to the wearable device via the communication device the notification for presentation by the wearable device,
wherein the notification includes a message recommending ending of the sedentary activity level, and
wherein the communication device is configured to send the notification at another time of the day.

11. The method of claim 9, further comprising:
detecting a third time period for which a number of consecutive samples have been classified into the non-sedentary status;
determining that the third time period is greater than a second threshold time period; and
classify the third time period as having a non-sedentary state upon determining that the third time period is greater than the second threshold time period.

12. The method of claim 11, further comprising:
determining that the third time period is contiguous with a time period that has been classified as having the sedentary state;
identifying a transition from the sedentary state to the non-sedentary state upon determining that the third time period is contiguous with the time period that has been classified as having the sedentary state; and
sending to the wearable device via the communication device a second notification including a motivational message for display via the wearable device upon identifying the transition from the sedentary state to the non-sedentary state.

13. The method of claim 9, further comprising:
determining that values of the samples of the motion measures for a group of consecutive moments of interest are each greater than the first predetermined threshold and each less than a second predetermined threshold, the second predetermined threshold being higher than the first predetermined threshold,
determining that a value of one of the samples of the motion measures for a moment of interest preceding the group of consecutive moments of interest is classified as having the sedentary status,
determining that a value of one of the samples of the motion measures for a moment of interest subsequent to the group of consecutive moments of interest is classified as having the sedentary status, and
classifying each of the samples of the motion measures for the group of consecutive moments of interest as having the sedentary status.

14. The method of claim 13, further comprising determining that a size of the group of consecutive moments of interest is less than a size threshold prior to the classifying each of the samples of the motion measures for the group of consecutive moments of interest as having the sedentary status.

15. The method of claim 13, wherein each of the samples of the motion measures is classified as having the sedentary status, the non-sedentary status, or an asleep status.

16. The method of claim 9, wherein the samples of the motion measures comprises at least one of a number of steps taken by the user or a number of floors climbed or descended by the user.

* * * * *